US012757878B2

(12) United States Patent
Wada et al.

(10) Patent No.: US 12,757,878 B2

(45) Date of Patent: Oct. 13, 2026

(54) SYSTEM FOR DETECTING EXTRACELLULAR PURINERGIC RECEPTOR LIGAND, AND NON-HUMAN ANIMAL HAVING THE SYSTEM INTRODUCED THEREINTO

(71) Applicant: Chugai Seiyaku Kabushiki Kaisha, Tokyo (JP)

(72) Inventors: Manabu Wada, Kanagawa (JP); Naoko Wada, Shizuoka (JP); Otoya Ueda, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 857 days.

(21) Appl. No.: 17/784,735

(22) PCT Filed: Dec. 11, 2020

(86) PCT No.: PCT/JP2020/046301

§ 371 (c)(1),
(2) Date: Jun. 13, 2022

(87) PCT Pub. No.: WO2021/117874

PCT Pub. Date: Jun. 17, 2021

(65) Prior Publication Data

US 2023/0000063 A1 Jan. 5, 2023

(30) Foreign Application Priority Data

Dec. 13, 2019 (JP) ................................ 2019-225404

(51) Int. Cl.

| | |
|---|---|
| ***A01K 67/027*** | (2024.01) |
| ***C12N 5/10*** | (2006.01) |
| ***C12N 9/02*** | (2006.01) |
| ***C12N 15/62*** | (2006.01) |
| ***G01N 33/15*** | (2006.01) |
| ***G01N 33/50*** | (2006.01) |

(52) U.S. Cl.

CPC .............. *A01K 67/027* (2013.01); *C12N 5/10* (2013.01); *C12N 9/0004* (2013.01); *C12N 15/62* (2013.01); *G01N 33/15* (2013.01); *G01N 33/5088* (2013.01)

(58) Field of Classification Search

CPC ...... A01K 67/027; C12N 5/10; C12N 9/0004; C12N 15/62; G01N 33/15; G01N 33/5088

See application file for complete search history.

(56) References Cited

U.S. PATENT DOCUMENTS

| | | | |
|---|---|---|---|
| 2003/0215878 | A1 | 11/2003 | Eishingdrelo et al. |
| 2015/0119352 | A1 | 4/2015 | Miller et al. |
| 2018/0110880 | A1 | 4/2018 | Yamamoto |

FOREIGN PATENT DOCUMENTS

| | | | |
|---|---|---|---|
| CN | 1378593 | A | 11/2002 |
| JP | 2015-517565 | | 6/2015 |
| JP | 2019-92417 | A | 6/2019 |
| TV | 2004/02424 | A | 2/2004 |
| WO | WO 01/14539 | A2 | 3/2001 |
| WO | WO 2006/126231 | | 11/2006 |
| WO | WO 2015/108102 | | 7/2015 |
| WO | WO 2017/204318 | | 11/2017 |

OTHER PUBLICATIONS

Kavzmarek-Hajek, K., et al., "Re-evaluation of neuronal P2X7 expression using novel mouse models and a P2X7-specific nanobody," Elife 7: e36217. doi: 10.7554/eLife.36217. (Year: 2018).*

Jacobson, K., A., et al., "New paradigms in purinergic receptor ligand discovery," Neuropharmacology 230:109503. doi: 10.1016/j.neuropharm.2023. (Year: 2023).*

Yanagida, K., et al., "Identification and characterization of a novel lysophosphatidic acid receptor, p2y5/LPA6," J Biol Chem 284(26): 17731-1741. doi: 10.1074/jbc.M808506200. (Year: 2009).*

Noguchi, K., et al., "Identification of p2y9/GPR23 as a novel G protein-coupled receptor for lysophosphatidic acid, structurally distant from the Edg family," J Biol Chem 278(28): 25600-25606. doi: 10.1074/jbc.M302648200. (Year: 2003).*

Nonaka, Y., et al., "Identification of endogenous surrogate ligands for human P2Y12 receptors by in silico and in vitro methods," Biochem Biophys Res Commun 337(1): 281-288. doi: 10.1016/j.bbrc.2005.09.052. (Year: 2005).*

Conley, J. M., et al., "Imaging extracellular ATP with a genetically-encoded, ratiometric fluorescent sensor," PLoS One 12(11): e0187481. doi: 10.1371/journal.pone.0187481. (Year: 2017).*

Khalid, M., et al., "Carcinoma-specific expression of P2Y11 receptor and its contribution in ATP-induced purinergic signalling and cell migration in human hepatocellular carcinoma cells," Oncotarget 8(23):37278-37290. doi: 10.18632/oncotarget.16191. (Year: 2017).*

Jacobson, K. A., et al., "Update of P2Y receptor pharmacology: IUPHAR Review 27," Br J Pharmacol 177(11):2413-2433. doi: 10.1111/bph.15005. (Year: 2020).*

Ollivier M, Beudez J, Linck N, Grutter T, Compan V, Rassendren F. P2X-GCaMPs as versatile tools for imaging extracellular ATP signaling. bioRxiv. Apr. 24, 2020:Apr. 2020. (Year: 2020).*

Kono et al., "Bioluminescence imaging of G protein-coupled receptor activation in living mice," Nature Communications, Oct. 27, 2017, 8(1):1-11.

(Continued)

*Primary Examiner* — Robert M Kelly
*Assistant Examiner* — Eric J Rogers
(74) *Attorney, Agent, or Firm* — Fish & Richardson P.C.

(57) ABSTRACT

An object of the present invention is to provide an evaluation system capable of detecting an extracellular purinergic receptor ligand minimally invasively, chronologically and systemically, and the present invention provides a genetically modified non-human animal expressing a first fusion protein and a second fusion protein for detecting an extracellular purinergic receptor ligand, in which the first fusion protein comprises a membrane protein that binds to a purinergic receptor ligand, and a first reporter protein, and the second fusion protein comprises a protein that binds to the membrane protein bound to the ligand, and a second reporter protein; and a cell thereof.

18 Claims, 8 Drawing Sheets

Specification includes a Sequence Listing.

(56) References Cited

OTHER PUBLICATIONS

Storme, "β-Arrestin coupling to Purinergic Receptors: Glo with the Flow?," Faculty of Pharmaceutical Sciences, Dec. 18, 2018, pp. 1-216.
Takakura et al., "Visualization and Quantitative Analysis of G Protein-Coupled Receptor-β-Arrestin Interaction of Single Cells and Specific Organs of Living Mice Using Split Luciferase Complementation," ACS Chemical Biology, Mar. 12, 2012, 7(5):901-910.
Wang et al., "Techniques for detection of second messengers cAMP and cGMP," Journal of Food Science and Technology, Nov. 30, 2017, 35(6):48-54 (with English abstract).
Chinese Office Action in CN 202080086064.1, dated Oct. 28, 2023, 11 pages (with English translation).
Extended European Search Report in EP 20900121.3, dated Dec. 14, 2023, 9 pages.
Hoffman et al., "Agonist-selective, Receptor-specific Interaction of Human $P_{2Y}$ Receptors with β-Arrestin-1 and -2," The Journal of Biological Chemistry, Nov. 7, 2008, 283(45):30933-30941.
Storme et al., "Molecular dissection of the human $A_3$ adenosine receptor coupling with β-arrestin2," Biochemical Pharmacology, Jan. 5, 2018, 148:298-307.
Chinese Office Action in CN 202080086064.1, dated Apr. 26, 2024, 15 pages (with English translation).
Chu et al., "Ex vivo and in vivo fluorescence detection and imaging of adenosine triphosphate," J Nanobiotechnology, Jun. 22, 2021, 9(1):187, 12 pages.
Conley et al., "Imaging extracellular ATP with a genetically-encoded, ratiometric fluorescent sensor," Plos One, Nov. 9, 2017, 12(11):e0187481, 24 pages.
Di Virgilio et al., "Assessing Extracellular ATP as Danger Signal In Vivo: The pmeLuc System," Methods Mol Biol, 2016, 1417:115-129.
Faroqi et al., "In Vivo Detection of Extracellular Adenosine Triphosphate in a Mouse Model of Traumatic Brain Injury," J Neurotrauma, Feb. 19, 2021, 38(5):655-664.
Idzko et al., "Extracellular ATP triggers and maintains asthmatic airway inflammation by activating dendritic cells," Nat Med, Jul. 15, 2007, 13(8):913-919.
Kitajima et al., "Real-time in vivo imaging of extracellular ATP in the brain with a hybrid-type fluorescent sensor," eLife, Jul. 10, 2020, 9:e57544, 18 pages.
Lee et al., "A novel method using an acedan-based Zn(DPA) probe to monitor ATP localization in an in vivo system," J Mol Hist, Apr. 2013, 44(2):241-247.
Llaudet et al., "Microelectrode Biosensor for Real-Time Measurement of ATP in Biological Tissue," Anal Chem, May 15, 2005, 77(10):3267-3273.
Lommatzsch et al., "Extracellular Adenosine Triphosphate and Chronic Obstructive Pulmonary Disease," Am J Respir Crit Care Med, Jan. 21, 2010, 181(9):928-934.
Morciano et al., "Use of luciferase probes to measure ATP in living cells and animals," Nat Protoc, Aug. 2017, 12(8):1542-1562.
Pellegatti et al., "Increased Level of Extracellular ATP at Tumor Sites: In Vivo Imaging with Plasma Membrane Luciferase," Plos One, Jul. 9, 2008, 3(7):e2599, 9 pages.
Santos-Cancel et al., "Direct, Real-Time Detection of Adenosine Triphosphate Release from Astrocytes in 3-Dimensional Culture Using an Integrated Electrochemical, Aptamer-Based Sensor," ACS Chem Neurosci, Feb. 12, 2019, 10(4):2070-2079.
Welter-Stahl et al., "Expression of purinergic receptors and modulation of $P2X_7$ function by the inflammatory cytokine IFNγ in human epithelial cells," Biochimica et Biophysica Acta, Mar. 21, 2009, 1788(1):1176-1187.
International Search Report in PCT/JP2020/046301, mailed Feb. 9, 2021, 4 pages (with English translation).
Chinese Office Action in Chinese Application No. 202080086064.1, dated Mar. 18, 2025, 16 pages (with English translation).
Conn, "cAMP Biosensors Applied in Molecular Pharmacological Studies of G Protein-Coupled Receptors," Methods in Enzymology, Dec. 31, 2013, Chapter 11, 522:191-192.
Sitaramayya, Signal Transduction Pathways, Mechanisms and Diseases, Dec. 31, 2010, p. 96.

* cited by examiner

[Figure 1]
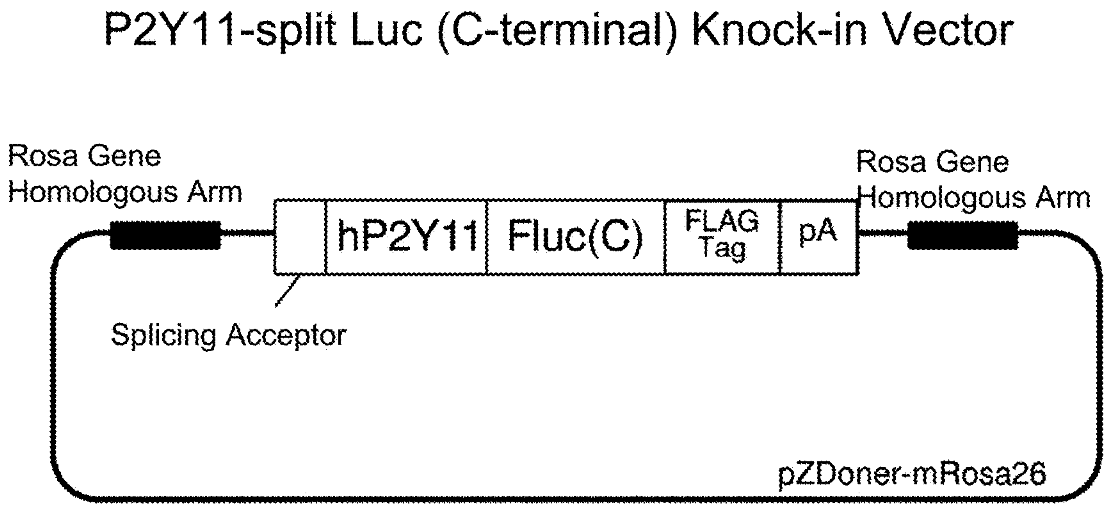
[Figure 2]
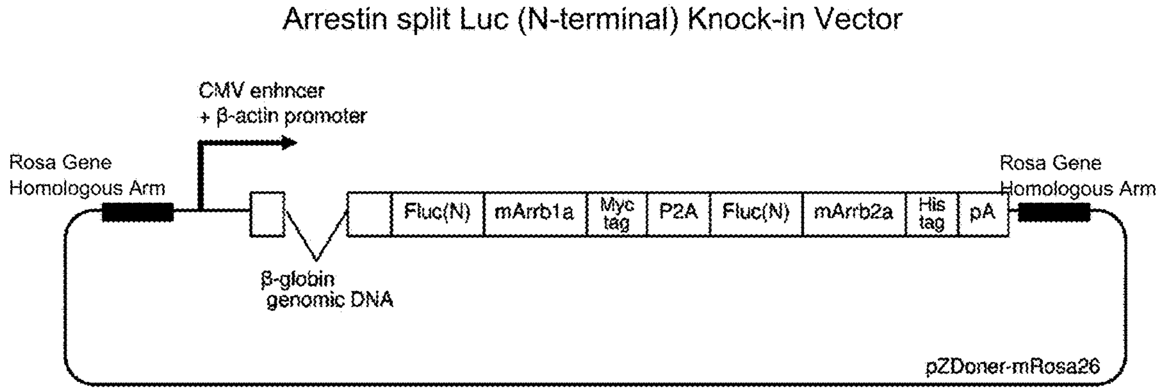

[Figure 3]
Luminescent Signal Detection in Double Knock-in Mice
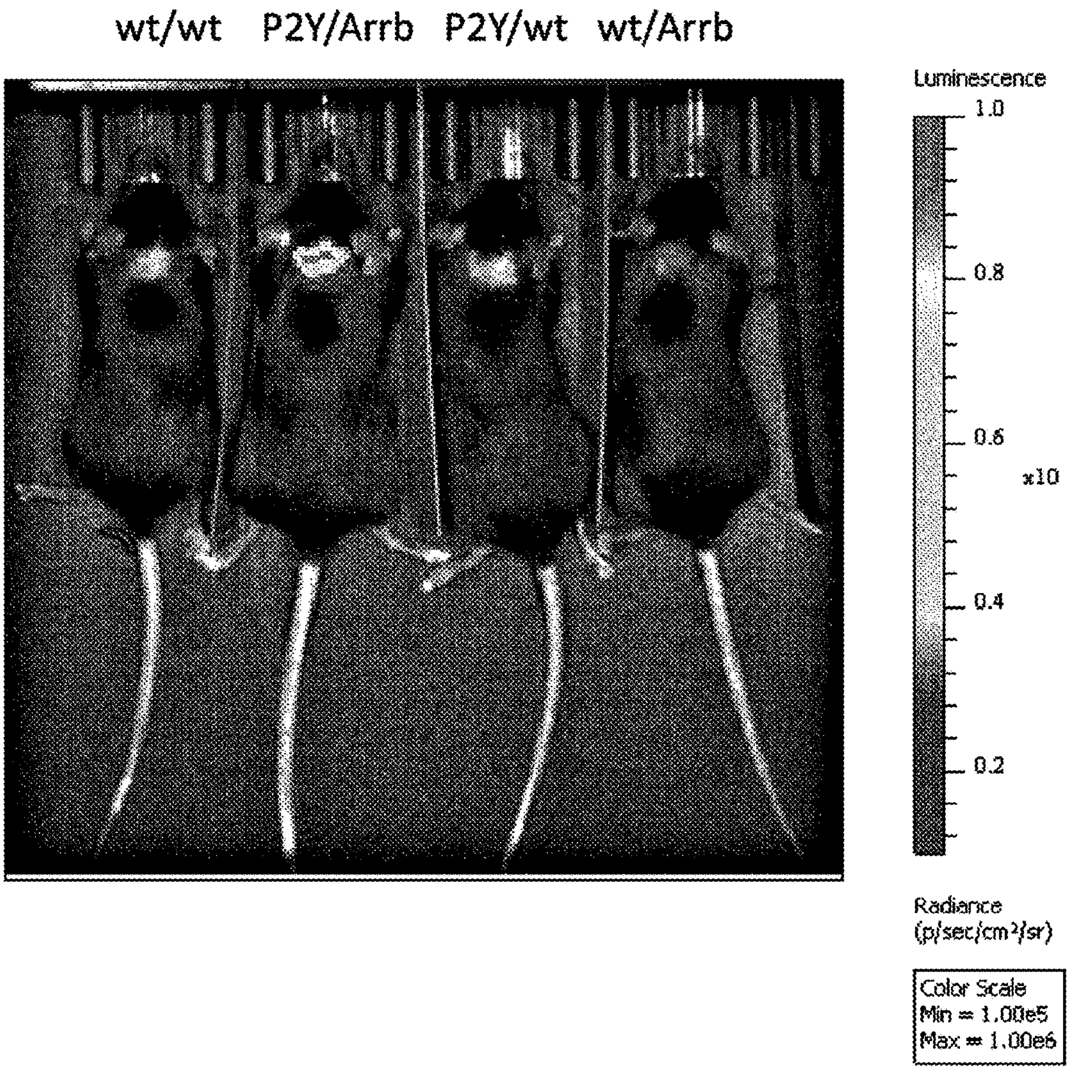

[Figure 4]
ATP Concentration-dependent Luminescent Signal Detection in Double Knock-in Mouse-derived Fibroblasts
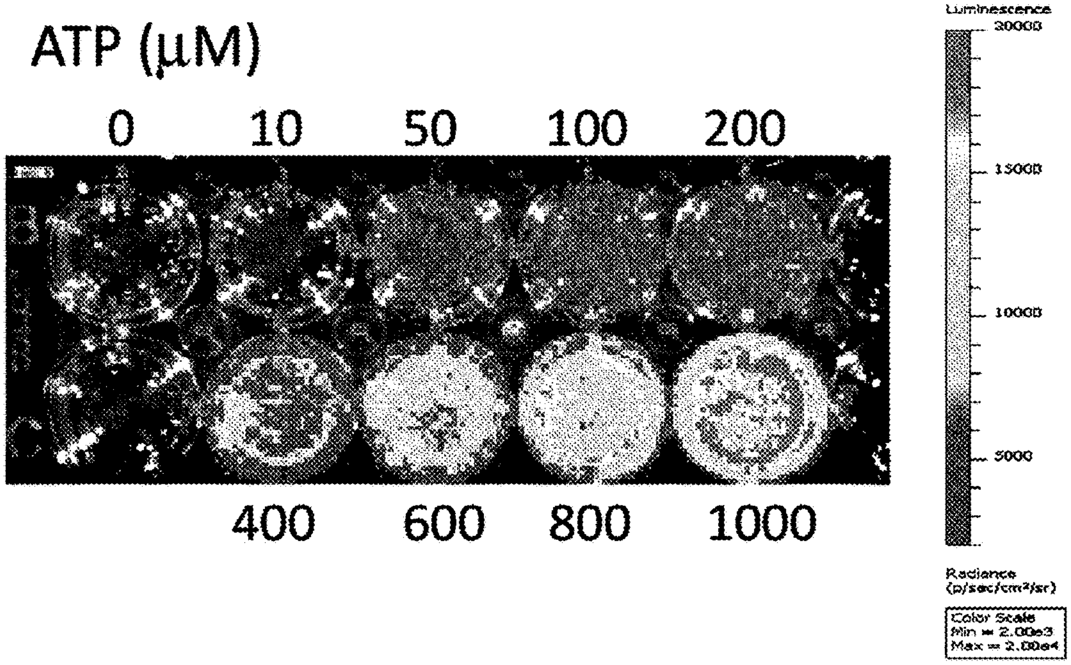

[Figure 5]
ATP Concentration-dependent Luminescent Signal Detection in Double Knock-in Mouse-derived Fibroblasts
*in vitro* ATP Concentration-dependent Detection
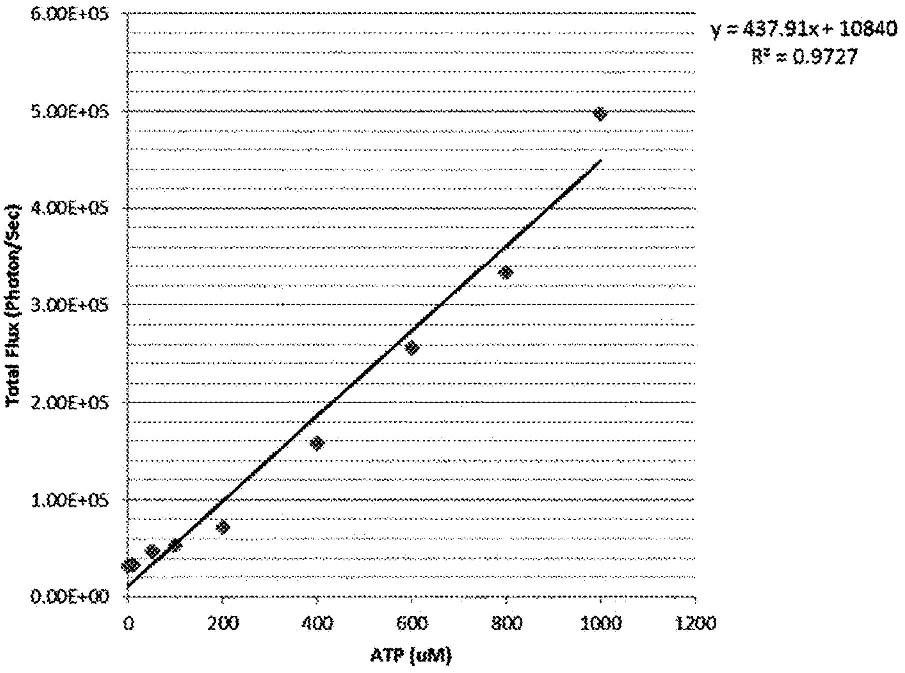

[Figure 6]
ATP Concentration-dependent Signal Detection in Double Knock-in Mice
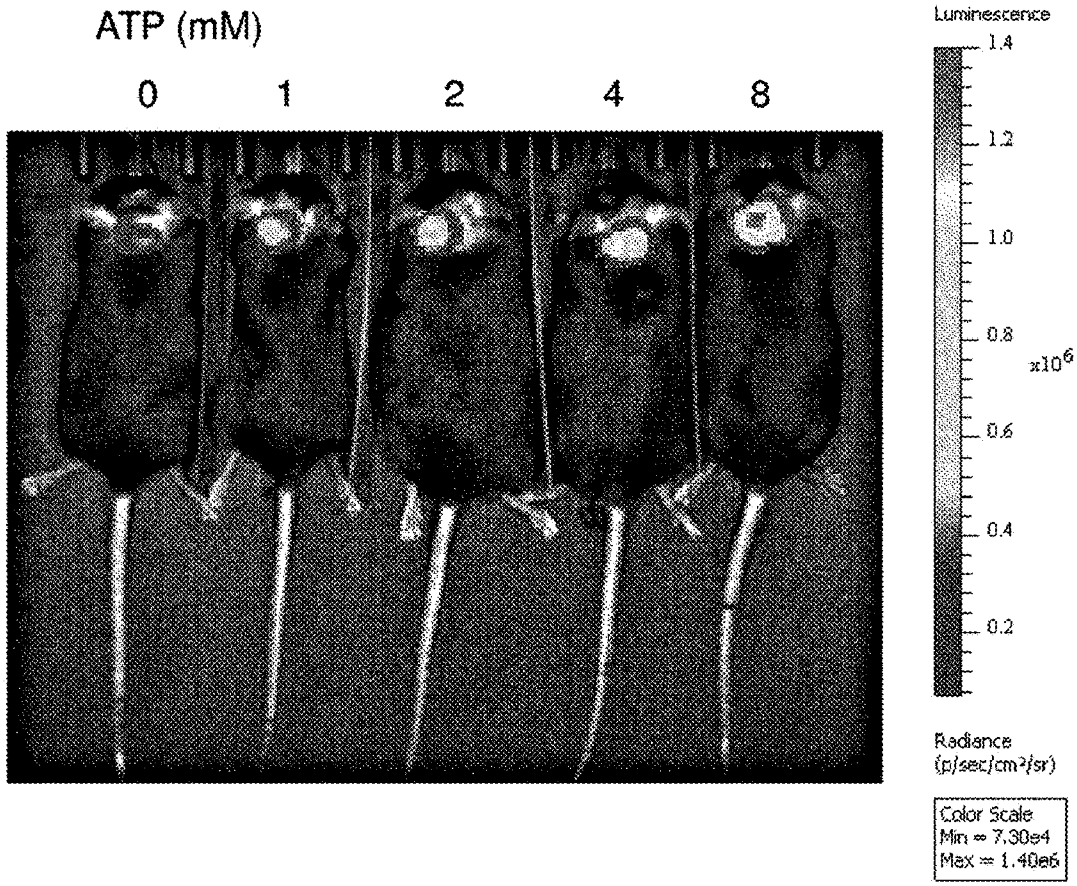

[Figure 7]
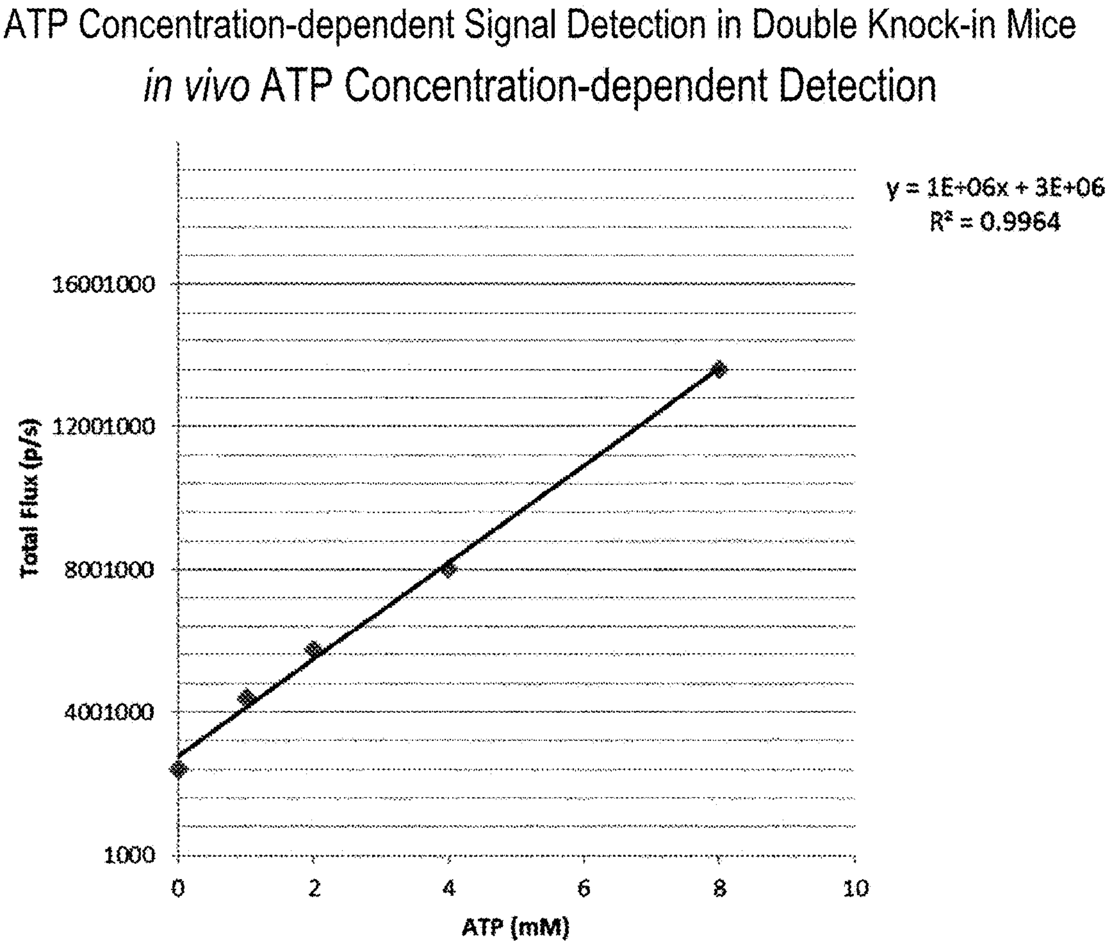

[Figure 8]
Detection in Double Knock-in Mice of ATP Derived from Damage in Liver Cells Caused by Hydrodynamic Injection
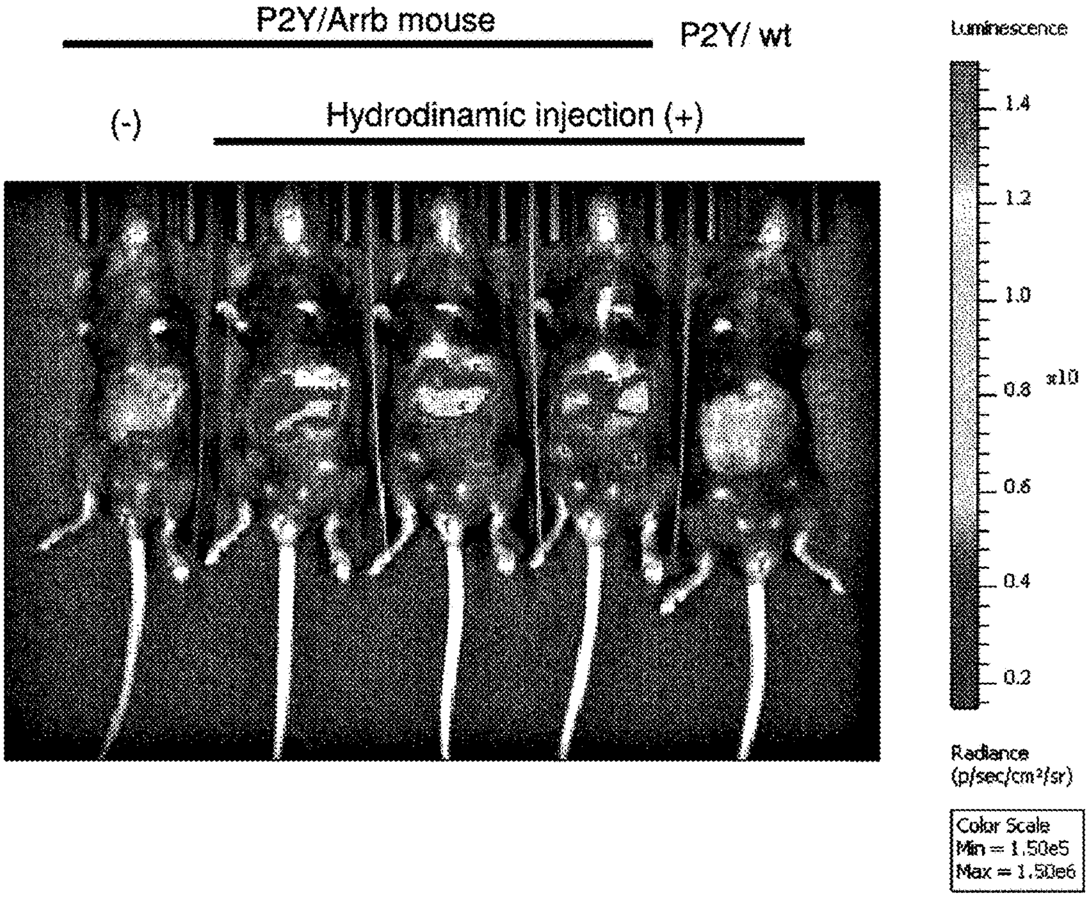

[Figure 9]
Detection in Double Knock-in Mice of ATP Derived from Canceration Caused by Hydrodynamic Injection
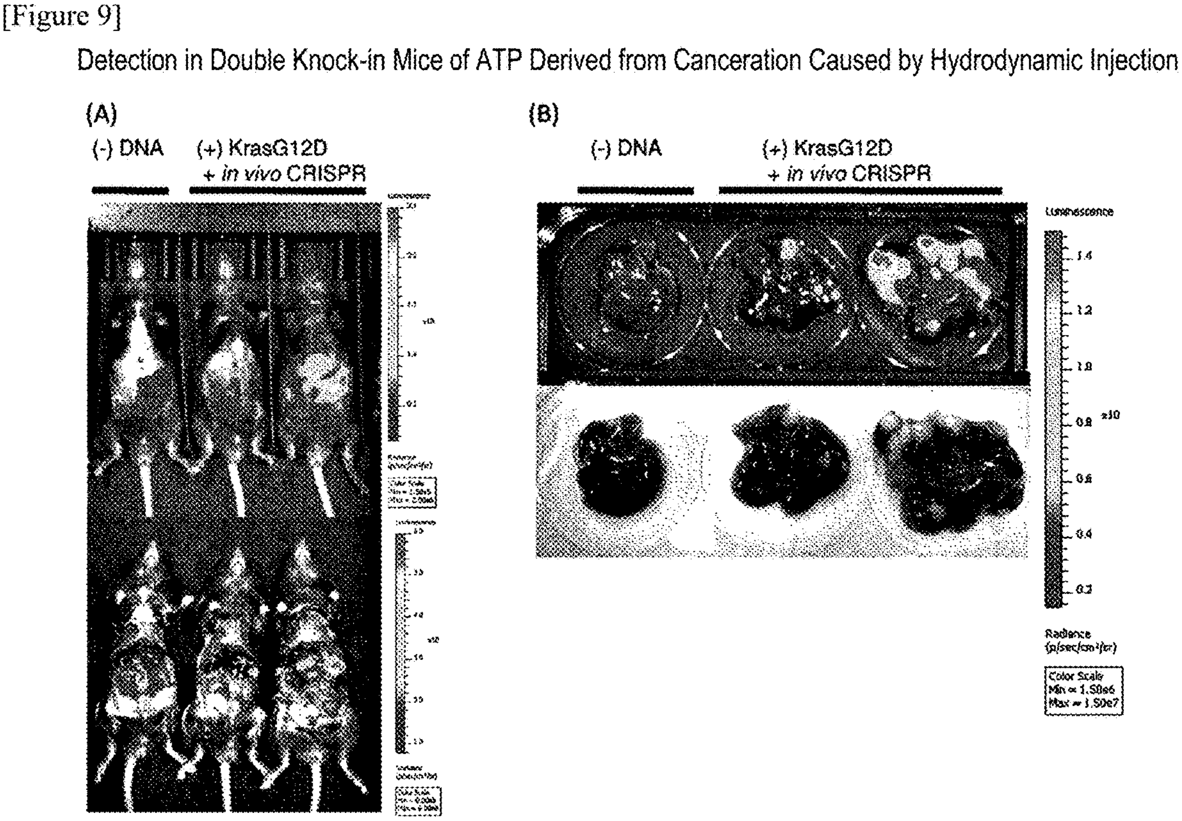

SYSTEM FOR DETECTING EXTRACELLULAR PURINERGIC RECEPTOR LIGAND, AND NON-HUMAN ANIMAL HAVING THE SYSTEM INTRODUCED THEREINTO

CROSS-REFERENCE TO RELATED APPLICATIONS

This application is the National Stage of International Application No. PCT/JP2020/046301, filed Dec. 11, 2020, which claims the benefit of Japanese Application No. 2019-225404, filed Dec. 13, 2019. SEQUENCE LISTING This application contains a Sequence Listing that has been submitted electronically as an ASCII text file named SequenceListing.txt. The ASCII text file, created on Dec. 11, 2020 and modified on Jun. 7, 2022, is 28.6 kilobytes in size. The material in the ASCII text file is hereby incorporated by reference in its entirety.

TECHNICAL FIELD

The present invention relates to a system for detecting an extracellular purinergic receptor ligand utilizing signal transduction of a receptor protein with a purinergic receptor ligand used as a ligand, and a genetically modified non-human animal having the system introduced thereinto. Besides, it relates to monitoring of a disease condition, a compound evaluation method and the like using a genetically modified non-human animal into which a system for detecting an extracellular purinergic receptor ligand has been introduced.

BACKGROUND ART

Purinergic receptors are a group of cell surface receptors using nucleotides such as adenosine and ATP as ligands. It has been reported that purinergic receptors are involved in various diseases including immune disorder, and purinergic receptor inhibitors and purinergic receptor agonists targeting purinergic receptors have been developed. As purinergic receptor ligands, nucleotides such as ATP, adenosine and metabolites thereof are known, and it has been reported that signaling pathways formed by these purinergic receptor ligands and purinergic receptors are involved in various physiological phenomena such as neurotransmission, muscle contraction, a sense of pain, a sense of taste, and an inflammatory reaction.

The purinergic receptor ligands such as ATP and adenosine function as signal transducers in a living body, and hence attempts have been made to verify their behaviors such as production and decomposition in a living body, and to measure their concentrations. As an example, it is known that a large amount of intracellular ATP is leaked out of cells along with cell death, which has been reported to play a role as a significant danger signal in inflammatory process. Besides, in a cancer tissue, a large amount of intracellular ATP is leaked out of cells when cancer cells die, and it has been reported that an ATP concentration in a cancer tissue is higher than in a normal tissue (Non Patent Literatures 1, 3 and 4).

An example of a method for measuring an intravital substance including an extracellular purinergic receptor ligand of a living body includes a microdialysis method. In this method, a tissue liquid or an extracellular liquid collected from a tissue is analyzed by using HPLC or the like. When a measurement target is ATP, a measurement method by luciferin-luciferase assay may be employed apart from the analysis method by HPLC or the like. Even when this method is employed, however, it is difficult to definitely determine whether a detected/measured purinergic receptor ligand is of intracellular origin or extracellular origin, and a purinergic receptor ligand concentration in a living body cannot be measured in real time. Besides, in the microdialysis method, a tissue liquid is collected by inserting a needle into a tissue, and at this point, cell death or tissue necrosis may occur in the insertion site. In such a case, there arises a problem that an artifact derived from the measurement method affects a measurement result. When a substance to be measured is ATP, it is known to be secreted along with cell death or a cell inflammatory reaction, and hence the measurement by this method is more unsuitable. Patent Literature 2 reports a method for observing an ATP distribution and variation in a living body by using a non-human mammal expressing a fusion protein in which two fluorescent proteins workable as a donor and an acceptor in fluorescence resonance energy transfer are respectively bound on an amino terminal side and a carboxy terminal side of ε subunit of ATP synthase. This method, however, focuses on intracellular ATP, and cannot evaluate extracellular ATP.

Besides, as an attempt to measure extracellular ATP in a living body, a method using a genetically modified cell having luciferase extracellularly expressed has been reported (Non Patent Literatures 1 and 2, and Patent Literature 1). In this method, the genetically modified cell emits a signal through a luciferin-luciferase reaction when exposed to an environment having a high concentration of extracellular ATP, and the signal is detected for measuring extracellular ATP in a living body. In this method, however, it is necessary to transfer the cell in a living body, and it is difficult to distribute the transferred cell systemically over the living body, and there remains a problem that if it is unknown when ATP is extracellularly released, it is difficult to determine when the cell should be transferred. The method also has a problem that it cannot be employed if the transferred cell is eliminated by the host immune system. Besides, it is only ATP that can be measured through the luciferin-luciferase reaction, and other purinergic receptor ligands cannot be measured.

Although not only ATP but also the other purinergic receptor ligands have been reported to be involved in various diseases as extracellular signal transducers, there are many unclear points about which extracellular purinergic receptor ligand functions how and for which disease at which timing. Therefore, for evaluation of the function of an extracellular purinergic receptor ligand in a living body and in a disease condition, an evaluation system capable of detecting an extracellular purinergic receptor ligand minimally invasively, chronologically and systemically is necessary, but such an evaluation system does not still exist.

CITATION LIST

Patent Literature

[Patent Literature 1] WO 2006/126231

[Patent Literature 2] WO 2015/108102

Non Patent Literature

[Non Patent Literature 1] Patrizia et. al., (2008) PLoS One. 3, e2599

[Non Patent Literature 2] Francesco Di Virgilio et. al., (2016), Methods Mol Biol. 1417, 115-29

[Non Patent Literature 3] Idzko M et. al., (2007) Nat Med. August; 13 (8): 913-9

[Non Patent Literature 4] Lommatzsch M et. al., (2010) Am J Respir Crit Care Med. May 1; 181 (9): 928-34

SUMMARY OF INVENTION

Technical Problem

The present invention was devised in consideration of the above-described circumstances, and an object is to provide an evaluation system capable of detecting an extracellular purinergic receptor ligand minimally invasively, chronologically and systemically. More specifically, objects of the present invention are to provide a genetically modified non-human animal systemically expressing a reporter protein for detecting/evaluating an extracellular purinergic receptor ligand, and to construct an evaluation system for detecting an extracellular purinergic receptor ligand. Another object of the present invention is to provide a method, using the evaluation system for detecting an extracellular purinergic receptor ligand using the genetically modified non-human animal and the reporter protein, for detecting various diseases and monitoring disease conditions of the various diseases, and for screening for therapeutic agents for these diseases.

Solution to Problem

The present inventors made earnest studies to solve the above-described problems, and have found as a result that a P2Y purinergic receptor and β-Arrestin which intracellularly binds thereto are fused with respective subunit proteins of split luciferase to produce a genetically modified mouse systemically expressing these, and thus, extracellular ATP can be detected. In other words, according to this genetic modification, when extracellular ATP binds to the P2Y receptor, the P2Y receptor binds to β-Arrestin in a cell, and the subunit proteins fused thereto are appropriately assembled to reconstruct/generate luciferase. Luciferase can express a luminescent signal in the presence of an appropriate substrate, and extracellular ATP can be detected by detecting this signal. Besides, it was confirmed that when ATP measurement is performed using a cell isolated from the genetically modified mouse, a luminescent signal intensity thus detected is concentration dependent, and thus an ATP concentration can be quantitatively measured. Therefore, the present invention is also applicable to ATP concentration measurement and screening in vitro. Besides, detection of extracellular ATP in a living body of the genetically modified mouse was examined, and as a result, it was found that the luminescent signal can be detected in a concentration dependent manner, and hence systemic extracellular ATP can be thus detected non-invasively and chronologically.

The present invention was accomplished based on these findings, and relates to, for example, the following inventions in specific aspects.

[1] A genetically modified non-human animal expressing a first fusion protein and a second fusion protein for detecting an extracellular purinergic receptor ligand, wherein the first fusion protein comprises a membrane protein that binds to a purinergic receptor ligand, and a first reporter protein, and the second fusion protein comprises a protein that binds to the membrane protein bound to the ligand, and a second reporter protein.

[2] The genetically modified non-human animal according to [1], wherein the first reporter protein and the second reporter protein are respective subunits of a split reporter protein.

[3] The genetically modified non-human animal according to [2], wherein the split reporter protein is split luciferase.

[4] The genetically modified non-human animal according to [2], wherein the split reporter protein is a split fluorescent protein.

[5] The genetically modified non-human animal according to [1], wherein the first reporter protein and the second reporter protein are a combination of proteins causing fluorescence resonance energy transfer (FRET) or bioluminescence resonance energy transfer (BRET).

[6] The genetically modified non-human animal according to any one of [1] to [5], wherein the protein that binds to the membrane protein bound to the ligand is Arrestin or a portion thereof.

[7] The genetically modified non-human animal according to any one of [1] to [6], wherein the membrane protein is a G protein-coupled receptor (GPCR) or a portion thereof.

[8] The genetically modified non-human animal according to [7], wherein the GPCR is a P1 receptor.

[9] The genetically modified non-human animal according to [8], wherein the P1 receptor is selected from the group consisting of an adenosine A1 receptor, an adenosine A2A receptor, an adenosine A2B receptor, and an adenosine A3 receptor.

[10] The genetically modified non-human animal according to [8] or [9], wherein the purinergic receptor ligand is a P1 receptor ligand.

[11] The genetically modified non-human animal according to [10], wherein the P1 receptor ligand is selected from the group consisting of adenosine, AMP, ADP, and ATP.

[12] The genetically modified non-human animal according to [7], wherein the GPCR is a P2 receptor.

[13] The genetically modified non-human animal according to [12], wherein the P2 receptor is a P2Y receptor.

[14] The genetically modified non-human animal according to [13], wherein the P2Y receptor is selected from the group consisting of P2Y1, P2Y2, P2Y4B, P2Y6, P2Y11, P2Y12, P2Y13, and P2Y14.

[15] The genetically modified non-human animal according to any one of [12] to [14], wherein the purinergic receptor ligand is a P2 receptor ligand.

[16] The genetically modified non-human animal according to [15], wherein the P2 receptor ligand is a molecule having a nucleotide skeleton.

[17] The genetically modified non-human animal according to [15] or [16], wherein the P2 receptor ligand is selected from the group consisting of AMP, ADP, ATP, UTP, UDP, and UDP glucose.

[18] The genetically modified non-human animal according to any one of [15] to [17], wherein the P2 receptor ligand is ATP.

[19] The genetically modified non-human animal according to any one of [1] to [18], wherein the first fusion protein and the second fusion protein are systemically expressed.

[20] The genetically modified non-human animal according to any one of [1] to [19], wherein the non-human animal is a non-human mammal.

[21] The genetically modified non-human animal according to [20], wherein the non-human animal is a rodent.

[22] The genetically modified non-human animal according to [20] or [21], wherein the non-human animal is a mouse.

[23] The genetically modified non-human animal according to any one of [1] to [22], being a disease model animal.

[24] The genetically modified non-human animal according to [23], wherein a disease is selected from the group consisting of cancer, acute inflammation, chronic inflammation, infectious diseases, fibrosis, physical or chemical organ lesion, and cell damage caused by an anticancer agent or the like.

[25] An animal cell expressing a first fusion protein and a second fusion protein for detecting an extracellular purinergic receptor ligand, wherein the first fusion protein comprises a membrane protein that binds to a purinergic receptor ligand, and a first reporter protein, and the second fusion protein comprises a protein that binds to the membrane protein bound to the ligand, and a second reporter protein.

[26] The animal cell according to [25], wherein the first reporter protein and the second reporter protein are respective subunits of a split reporter protein.

[27] The animal cell according to [26], wherein the split reporter protein is split luciferase.

[28] The animal cell according to [26], wherein the split reporter protein is a split fluorescent protein.

[29] The animal cell according to [25], wherein the first reporter protein and the second reporter protein are a combination of proteins causing fluorescence resonance energy transfer (FRET) or bioluminescence resonance energy transfer (BRET).

[30] The animal cell according to any one of [25] to [29], wherein the protein that binds to the membrane protein bound to the ligand is Arrestin or a portion thereof.

[31] The animal cell according to any one of [25] to [30], wherein the membrane protein is a G protein-coupled receptor (GPCR) or a portion thereof.

[32] The animal cell according to any one of [25] to [31], wherein the GPCR is a P1 receptor.

[33] The animal cell according to [32], wherein the P1 receptor is selected from the group consisting of an adenosine A1 receptor, an adenosine A2A receptor, an adenosine A2B receptor, and an adenosine A3 receptor.

[34] The animal cell according to [32] or [33], wherein the purinergic receptor ligand is a P1 receptor ligand.

[35] The animal cell according to [34], wherein the P1 receptor ligand is selected from the group consisting of adenosine, AMP, ADP, and ATP.

[36] The animal cell according to any one of [25] to [31], wherein the GPCR is P2 receptor.

[37] The animal cell according to [36], wherein the P2 receptor is a P2Y receptor.

[38] The animal cell according to [37], wherein the P2Y receptor is selected from the group consisting of P2Y1, P2Y2, P2Y4B, P2Y6, P2Y11, P2Y12, P2Y13, and P2Y14.

[39] The animal cell according to [37] or [38], wherein the purinergic receptor ligand is a P2 receptor ligand.

[40] The animal cell according to [39], wherein the P2 receptor ligand is a molecule having a nucleotide skeleton.

[41] The animal cell according to [39] or [40], wherein the P2 receptor ligand is selected from the group consisting of AMP, ADP, ATP, UTP, UDP, and UDP glucose.

[42] The animal cell according to any one of [39] to [41], wherein the P2 receptor ligand is ATP.

[43] The animal cell according to any one of [25] to [42], wherein the animal is a mammal.

[44] The animal cell according to any one of [25] to [43], wherein the animal is a rodent.

[45] The animal cell according to any one of [25] to [44], wherein the animal is a mouse.

[46] A detection kit for detecting an extracellular purinergic receptor ligand, comprising the animal cell according to any one of [25] to [45].

[47] A method for producing a genetically modified animal cell for detecting an extracellular purinergic receptor ligand, comprising: a step of introducing, into a genome, a gene encoding a first fusion protein comprising a membrane protein that binds to an extracellular purinergic receptor ligand, and a first reporter protein; and a step of introducing, into a genome, a gene encoding a second fusion protein comprising a protein that binds to the membrane protein bound to the ligand, and a second reporter protein.

[48] The production method according to [47], wherein the first reporter protein and the second reporter protein are respective subunits of a split reporter protein.

[49] The production method according to [48], wherein the split reporter protein is split luciferase.

[50] The production method according to [48], wherein the split reporter protein is a split fluorescent protein.

[51] The production method according to [47], wherein the first reporter protein and the second reporter protein are a combination of proteins causing fluorescence resonance energy transfer (FRET) or bioluminescence resonance energy transfer (BRET).

[52] The production method according to any one of [47] to [51], wherein the protein that binds to the membrane protein bound to the ligand is Arrestin or a portion thereof.

[53] The production method according to any one of [47] to [52], wherein the membrane protein is a G protein-coupled receptor (GPCR) or a portion thereof.

[54] The production method according to [53], wherein the GPCR is a P1 receptor.

[55] The production method according to [54], wherein the P1 receptor is selected from the group consisting of an adenosine A1 receptor, an adenosine A2A receptor, an adenosine A2B receptor, and an adenosine A3 receptor.

[56] The production method according to [54] or [55], wherein the purinergic receptor ligand is a P1 receptor ligand.

[57] The production method according to [56], wherein the P1 receptor ligand is selected from the group consisting of adenosine, AMP, ADP, and ATP.

[58] The production method according to [53], wherein the GPCR is a P2 receptor.

[59] The production method according to [58], wherein the P2 receptor is a P2Y receptor.

[60] The production method according to [59], wherein the P2Y receptor is selected from the group consisting of P2Y1, P2Y2, P2Y4B, P2Y6, P2Y11, P2Y12, P2Y13, and P2Y14.

[61] The production method according to any one of [58] to [60], wherein the purinergic receptor ligand is a P2 receptor ligand.

[62] The production method according to [61], wherein the P2 receptor ligand is a molecule having a nucleotide skeleton.

[63] The production method according to [61] or [62], wherein the P2 receptor ligand is selected from the group consisting of AMP, ADP, ATP, UTP, UDP, and UDP glucose.

[64] The production method according to any one of [61] to [63], wherein the P2 receptor ligand is ATP.

[65] The production method according to any one of [47] to [64], wherein the first fusion protein and the second fusion protein are systemically expressed.

[66] The production method according to any one of [47] to [65], wherein the animal cell is a mammal cell.

[67] The production method according to any one of [47] to [66], wherein the animal cell is a rodent cell.

[68] The production method according to any one of [47] to [67], wherein the animal cell is a mouse cell.

[69] The production method according to any one of [47] to [68], comprising detecting a reporter protein, and performing screening based on an amount thereof detected.

[70] A method for producing a genetically modified non-human animal for detecting an extracellular purinergic receptor ligand, comprising: a step of introducing, into a genome, a gene encoding a first fusion protein comprising a membrane protein that binds to an extracellular purinergic receptor ligand, and a first reporter protein; and a step of introducing, into a genome, a gene encoding a second fusion protein comprising a protein that binds to the membrane protein bound to the ligand, and a second reporter protein.

[71] The production method according to [70], wherein the first reporter protein and the second reporter protein are respective subunits of a split reporter protein.

[72] The production method according to [71], wherein the split reporter protein is split luciferase.

[73] The production method according to [71], wherein the split reporter protein is a split fluorescent protein.

[74] The production method according to [70], wherein the first reporter protein and the second reporter protein are a combination of proteins causing fluorescence resonance energy transfer (FRET) or bioluminescence resonance energy transfer (BRET).

[75] The production method according to any one of [70] to [74], wherein the protein that binds to the membrane protein bound to the ligand is Arrestin or a portion thereof.

[76] The production method according to any one of [70] to [75], wherein the membrane protein is a G protein-coupled receptor (GPCR) or a portion thereof.

[77] The production method according to [76], wherein the GPCR is a P1 receptor.

[78] The production method according to [77], wherein the P1 receptor is selected from the group consisting of an adenosine A1 receptor, an adenosine A2A receptor, an adenosine A2B receptor, and an adenosine A3 receptor.

[79] The production method according to [77] or [78], wherein the purinergic receptor ligand is a P1 receptor ligand.

[80] The production method according to any one of [77] to [79], wherein the P1 receptor ligand is selected from the group consisting of adenosine, AMP, ADP, and ATP.

[81] The production method according to [76], wherein the GPCR is a P2 receptor.

[82] The production method according to [81], wherein the P2 receptor is a P2Y receptor.

[83] The production method according to [82], wherein the P2Y receptor is selected from the group consisting of P2Y1, P2Y2, P2Y4B, P2Y6, P2Y11, P2Y12, P2Y13, and P2Y14.

[84] The production method according to any one of [81] to [83], wherein the purinergic receptor ligand is a P2 receptor ligand.

[85] The production method according to [84], wherein the P2 receptor ligand is a molecule having a nucleotide skeleton.

[86] The production method according to [84] or [85], wherein the P2 receptor ligand is selected from the group consisting of AMP, ADP, ATP, UTP, UDP, and UDP glucose.

[87] The production method according to any one of [84] to [86], wherein the P2 receptor ligand is ATP.

[88] The production method according to any one of [70] to [87], wherein the first fusion protein and the second fusion protein are systemically expressed.

[89] The production method according to any one of [70] to [88], wherein the non-human animal is a non-human mammal.

[90] The production method according to any one of [70] to [89], wherein the non-human animal is a rodent.

[91] The production method according to any one of [70] to [90], wherein the non-human animal is a mouse.

[92] The production method according to any one of [70] to [91], comprising detecting a reporter protein, and performing screening based on an amount thereof detected.

[93] A method for detecting an onset site of a disease, comprising a step of detecting a reporter protein in the genetically modified non-human animal according to [23] or [24].

[94] A method for detecting an onset time of a disease, comprising a step of detecting a reporter protein in the genetically modified non-human animal according to [23] or [24].

[95] A method for monitoring course of a disease, comprising a step of detecting a reporter protein in the genetically modified non-human animal according to [23] or [24].

[96] A method for evaluating a medicinal effect of a preventive agent for a disease or a disease therapeutic agent, comprising a step of administering the preventive agent or the disease therapeutic agent to the genetically modified non-human animal according to [23] or [24], and evaluating the medicinal effect of the preventive agent or the disease therapeutic agent based on a difference in an amount of a reporter protein detected between before and after the administration.

[97] A method for evaluating toxicity of a preventive agent for a disease or a disease therapeutic agent, comprising a step of administering the preventive agent or the disease therapeutic agent to the genetically modified non-human animal according to [23] or [24], and evaluating the toxicity of the preventive agent or the disease therapeutic agent based on a difference in an amount of a reporter protein detected between before and after the administration.

[98] A method for screening for a preventive agent for a disease or a disease therapeutic agent, comprising a step of administering a test substance to the genetically modified non-human animal according to [23] or [24], and screening for a substance effective for preventing or treating the disease based on a difference in an amount of a reporter protein detected between before and after the administration.

[99] A method for evaluating an effect of a medicinal molecule with a purinergic receptor ligand used as an index, comprising a step of administering the medicinal molecule to the genetically modified non-human animal according to any one of [1] to [24], or adding the medicinal molecule to the genetically modified animal cell according to any one of [25] to [45], and evaluating the effect of the medicinal molecule based on a difference in an amount of a reporter protein detected between before and after the administration or addition.

[100] A method for evaluating toxicity of a medicinal molecule with a purinergic receptor ligand used as an index, comprising a step of administering the medicinal molecule to the genetically modified non-human animal according to any one of [1] to [24], or adding the medicinal molecule to the genetically modified animal cell according to any one of [25] to [45], and evaluating the toxicity of the medicinal molecule based on a difference in an amount of a reporter protein between detected before and after the administration or addition.

[101] A method for evaluating an effect of a purinergic receptor ligand-dependent medicinal molecule, comprising a step of administering the drug to the genetically modified non-human animal according to any one of [1] to [24], or adding the medicinal molecule to the genetically modified animal cell according to any one of [25] to [45], and evaluating the effect of the medicinal molecule in the presence of a purinergic receptor ligand indicated by an amount of a reporter protein detected.

[102] A method for screening for a purinergic receptor ligand-dependent medicinal molecule, comprising a step of administering a test substance to the genetically modified non-human animal according to any one of [1] to [24], or adding the medicinal molecule to the genetically modified animal cell according to any one of [25] to [45], and screening for a target substance based on an effect of the medicinal molecule in the presence of a purinergic receptor ligand indicated by an amount of a reporter protein detected.

Advantageous Effects of Invention

According to the present invention, an evaluation system capable of detecting an extracellular purinergic receptor ligand minimally invasively, chronologically and systemically can be provided.

The present invention can provide a genetically modified non-human animal capable of detecting a systemic purinergic receptor ligand non-invasively and chronologically, and when the genetically modified non-human animal of the present invention is used, a cause site of a disease in which the purinergic receptor ligand is involved can be identified, or an onset time of the disease can be examined, and the mouse is also applicable to drug screening. Therefore, a therapeutic agent for a disease in which a purinergic receptor ligand is involved can be efficiently developed.

BRIEF DESCRIPTION OF DRAWINGS

FIG. 1 illustrates the outline of a P2Y11-split Luc (C-terminal) knock-in vector.

FIG. 2 illustrates the outline of an Arrestin-split Luc (N-terminal) knock-in vector.

FIG. 3 presents a photograph illustrating results of luminescent signal intensity measurement with a mixture of ATP and a D-luciferin substrate solution subcutaneously administered to P2Y11-split Luc (C-terminal) (P2Y)/Arrestin-split Luc (N-terminal) (Arrb) double knock-in mice. P2Y: P2Y11-split Luc (C-terminal) knock-in, Arrb: Arrestin-split Luc (N-terminal) knock-in, wt: wild type FIG. 4 presents an analysis data obtained by visualizing a luminescent signal detected by treatment of fibroblasts derived from a P2Y11-split Luc (C-terminal)/Arrestin-split Luc (N-terminal) double knock-in mouse with various concentrations of ATP and D-luciferin substrate.

FIG. 5 presents a graph illustrating luminescent signal intensity detected by treatment of fibroblasts derived from a P2Y11-split Luc (C-terminal)/Arrestin-split Luc (N-terminal) double knock-in mouse with various concentrations of ATP and D-luciferin substrate.

FIG. 6 presents a photograph illustrating results of luminescent signal intensity measured with mixtures of various concentrations of ATP and D-luciferin substrate solution subcutaneously administered to P2Y11-split Luc (C-terminal) (P2Y)/Arrestin-split Luc (N-terminal) (Arrb) double knock-in mice.

FIG. 7 presents a graph illustrating luminescent signal intensity measured with mixtures of various concentrations of ATP and D-luciferin substrate solution subcutaneously administered to P2Y11-split Luc (C-terminal) (P2Y)/Arrestin-split Luc (N-terminal) (Arrb) double knock-in mice.

FIG. 8 presents a photograph illustrating results obtained by non-invasively visualizing, through luminescent signal intensity measurement, ATP leakage in the liver, due to liver cell damage caused by hydrodynamic injection, in P2Y11-split Luc (C-terminal) (P2Y)/Arrestin-split Luc (N-terminal) (Arrb) double knock-in mice.

FIG. 9 presents ATP leakage due to canceration in the liver caused by hydrodynamic injection in P2Y11-split Luc (C-terminal) (P2Y)/Arrestin-split Luc (N-terminal) (Arrb) double knock-in mice obtained as results non-invasively visualized through luminescent signal intensity (A), and as results visualized through luminescent signal intensity measurement in the excised liver (B).

DESCRIPTION OF EMBODIMENT

1. Genetically Modified Non-Human Animal

The present invention relates to a genetically modified non-human animal expressing a first fusion protein and a second fusion protein for detecting an extracellular purinergic receptor ligand.

(1-1) First Fusion Protein

In the present invention, the "first fusion protein" comprises or consists of a membrane protein that binds to a purinergic receptor ligand, and a first reporter protein.

In the first fusion protein, the membrane protein that binds to a purinergic receptor ligand and the first reporter protein may be directly linked to each other, or may be linked via a linker. The membrane protein that binds to a purinergic receptor ligand and the first reporter protein can be linked in an arbitrary order as long as the first fusion protein and the second fusion protein can interact with each other as described below. In one aspect, the membrane protein that binds to a purinergic receptor ligand and the first reporter protein can be linked in the stated order from the N-terminal. As the "linker", an arbitrary one of conventionally known linkers can be used, and for example, a peptide linker can be used. The number of amino acids and the type of the peptide linker are not especially limited.

(1-1-1) Membrane Protein that Binds to Purinergic Receptor Ligand

In the present invention, the "membrane protein that binds to a purinergic receptor ligand" (hereinafter sometimes simply referred to as the "membrane protein") means a protein that is bound to a cell membrane or penetrates a cell membrane, and can bind to an extracellular purinergic receptor ligand. In the present invention, the membrane protein is not particularly limited as long as it can bind to an extracellular purinergic receptor ligand, and a G protein-coupled receptor (hereinafter referred to as "GPCR") that is a purinergic receptor, a ligand-gated ion channel receptor, or a portion of these can be suitably used. The membrane protein is preferably a GPCR that is a purinergic receptor.

A GPCR is mainly a seven transmembrane receptor, and has a structure in which seven a helix structures penetrate cytoplasm membrane, the N-terminal region is extracellularly positioned, and the C-terminal region is intracellularly positioned. When a ligand binds to the extracellular region, the GPCR is activated to be changed in the structure, and the intracellular region is phosphorylated owing to the action of G protein-coupled receptor kinase.

Examples of the GPCR that is a purinergic receptor include, but are not limited to, a P1 receptor and a P2 receptor. The membrane protein is preferably a P1 receptor and a P2 receptor.

The P1 receptor that is a purinergic receptor is a GPCR using adenosine, AMP, ADP, or ATP as a ligand, and can be classified into A1 receptors, A2A receptors, A2B receptors and A3 receptors. In the present invention, one of or a plurality of receptors selected from these can be used as the membrane protein.

The P2 receptor that is a purinergic receptor is a GPCR using AMP, ADP, ATP, UTP, UDP, or UDP glucose as a ligand, and is preferably a P2Y receptor. The P2Y receptor can be classified into $P2Y_1$ receptors, $P2Y_2$ receptors, $P2Y_4$B receptors, $P2Y_6$ receptors, $P2Y_{11}$ receptors, $P2Y_{12}$ receptors, $P2Y_{13}$ receptors, and $P2Y_{14}$ receptors. In the present invention, one of or a plurality of receptors selected from these can be used as the membrane protein. The $P2Y_2$ receptors and the $P2Y_{11}$ receptors having higher specificity to ATP are more preferred, and the $P2Y_{11}$ receptors are particularly preferred.

In the present invention, as the membrane protein that binds to a purinergic receptor ligand, any of known ones can be used, and known ones registered in public database such as NCBI and GenBank can be used. For example, as for the A1 receptors belonging to P1 receptor family, one derived from a human is registered as NP_000665.1, and one derived from a mouse is registered as NP_001008533.1, as for the P2Y2 receptors, one derived from a human is registered as NP_002555.3, and one derived from a mouse is registered as NP_001289275.1, and as for the $P2Y_{11}$ receptors, one derived from a human is registered as NP_002557.2. The membrane protein that binds to a purinergic receptor ligand is preferably derived from an animal of the same species as a host. In the present invention, for example, a $P2Y_{11}$ receptor represented by an amino acid sequence of SEQ ID NO: 9 can be used as the membrane protein that binds to a purinergic receptor ligand.

In the present invention, as the "membrane protein that binds to a purinergic receptor ligand", analogs and variants thereof can be used as long as they can bind to an extracellular purinergic receptor ligand. The analogs and variants of the "membrane protein that binds to a purinergic receptor ligand" means (i) a protein consisting of an amino acid sequence of the "membrane protein that binds to a purinergic receptor ligand" in which 1 to 50, for example, 1 to 20, or 1 to 10 amino acids are deleted, substituted, added or inserted, and capable of binding to an extracellular purinergic receptor ligand, or (ii) a protein consisting of an amino acid sequence having a sequence identity of 80% or more, preferably 90% or more, more preferably 95% or more, and still further preferably 99% or more with the amino acid sequence of the "membrane protein that binds to a purinergic receptor ligand", and capable of binding to an extracellular purinergic receptor ligand. The sequence identity of an amino acid sequence can be calculated based on a known method, and can be obtained by, for example, employing default settings of BLAST (Basic Local Alignment Search Tool at the National Center for Biological Information) or the like. The sequence identity of an amino acid sequence may be calculated based on the entire protein capable of binding to a purinergic receptor ligand, or may be calculated based on a binding domain having binding activity with a purinergic receptor ligand. For example, when a specific binding domain in a receptor that binds to a purinergic receptor ligand has a high sequence homology, it is understood that the specific binding domain has a high sequence homology even if the homology as the entire membrane protein is not high because a domain different from the binding domain, such as a transmembrane domain, has a low sequence homology.

The terms "portion of these" and "portion thereof" used in relation to the membrane protein in the present invention mean a protein consisting of an amino acid sequence of a part of the membrane protein, and capable of binding to an extracellular purinergic receptor ligand. An example of such a protein includes one containing at least a part of domains of the amino acid sequence of the membrane protein, such as a domain necessary for binding to at least an extracellular purinergic receptor ligand (such as a binding domain in a receptor binding to a specific purinergic receptor ligand) or a domain necessary for binding to a cell membrane (such as a transmembrane domain). Respective domains of the membrane protein can be determined based on amino acid sequence information and genetic information registered in public database such as NCBI and GenBank.

(1-1-2) First Reporter Protein

In the present invention, the "first reporter protein" means a protein functioning as a reporter protein together with the second reporter protein of the second fusion protein described below. The term "functioning as a reporter protein together" means that the function as a reporter protein is exhibited only when the first reporter protein and the second reporter protein are close or bound to each other, so as to work as an index indicating expression or localization of a specific molecule. Examples of such a protein "functioning as a reporter protein together" include a split reporter protein, and a combination of proteins causing fluorescence resonance energy transfer (FRET) or bioluminescence resonance energy transfer (BRET).

A "split reporter protein" refers to a reporter protein split into two or more subunits, and when the respective subunits are present to be away from one another, a function as a reporter protein is not exhibited, but when the split two or more subunits are close or bound to one another, a reporter protein is reconstructed and thus can exhibit the function. Regarding a "reporter protein split into subunits", a protein originally containing two or more subunits can be split into the respective subunits, and even a reporter protein originally containing one protein may be artificially split into a plurality of subunits. Examples of the reporter protein include, but are not limited to, green, red, blue or yellow fluorescent proteins, and enzymes such as luciferase, β-galactosidase, alkaline phosphatase, horseradish peroxidase, β-glucuronidase, chloramphenicol acetyl transferase, invertase, dihydrofolate acid reductase, and β-lactamase. A specific example of the split reporter protein includes split luciferase. Other specific examples include, but are not limited to, split fluorescent proteins such as split GFP, split YFP, and split CYP. Besides, it goes without saying that previously reported split reporter proteins can be used, and a specific reporter protein can be artificially split for use.

"FRET" means a phenomenon that when two fluorescent proteins, that is, a first fluorescent protein (donor) and a second fluorescent protein (acceptor) having a spectrum of a fluorescence wavelength of the former overlapping a spectrum of a wavelength of excitation light of the latter, are close to each other, energy absorbed through excitation of the first fluorescent protein is used as energy for excitation of the second fluorescent protein to cause the second fluorescent protein to emit fluorescence. Besides, "BRET" refers to a phenomenon that a bioluminescent protein is used instead of the first fluorescent protein (donor) of FRET, and when the bioluminescent protein and the second fluorescent protein are close to each other, energy generated at the time of bioluminescence of the bioluminescent protein is used as energy for excitation of the second fluorescent protein to cause the second fluorescent protein to emit fluorescence. An example of the bioluminescent protein include luciferase.

Accordingly, as the "first reporter protein" in the present invention, one subunit of a split reporter protein, one fluorescent protein in a combination of fluorescent proteins capable of causing FRET, or either protein of a combination of a bioluminescent protein and a fluorescent protein capable of causing BRET can be used.

(1-2) Second Fusion Protein

In the present invention, the "second fusion protein" comprises or consists of a protein capable of binding to the membrane protein bound to an extracellular purinergic receptor ligand (hereinafter sometimes referred to simply as the "protein capable of binding to the membrane protein bound to a ligand") and a second reporter protein.

In the second fusion protein, the protein capable of binding to the membrane protein bound to a ligand and the second reporter protein may be directly linked to each other, or may be linked via a linker. The protein capable of binding to the membrane protein bound to a ligand and the second reporter protein can be linked in an arbitrary order as long as the first fusion protein and the second fusion protein can interact with each other as described below. In one aspect, the second reporter protein and the protein capable of binding to the membrane protein bound to a ligand can be linked in the stated order from the N-terminal. As the "linker", an arbitrary one of conventionally known linkers can be used, and for example, a peptide linker can be used. The number of amino acids and the type of the peptide linker are not especially limited.

(1-2-1) Protein Capable of Binding to Membrane Protein Bound to Ligand

In the present invention, the "protein capable of binding to the membrane protein bound to an extracellular purinergic receptor ligand" means a protein capable of specifically or selectively binding to the above-described membrane protein bound to an extracellular purinergic receptor ligand. In the present invention, such a protein is not especially limited, and an activation regulator of a membrane protein, an antibody, a receptor kinase, a transcription factor, or a portion of these can be suitably used. In the present invention, when the membrane protein is GPCR, Arrestin that is an activation regulator of GPCR, G protein, or GPCR kinase can be suitably used.

"Arrestin" is an activation regulator that binds, in GPCR activated through a bond of a ligand in an extracellular region, to an intracellular region phosphorylated through action of G protein-coupled receptor kinase to cause desensitization of GPCR. It is known that four subtypes of Arrestin are present in mammals, which are Arrestin-1, Arrestin-2 (also designated as "β-Arrestin-1"), Arrestin-3 (also designated as "β-Arrestin-2"), and Arrestin-4 (also designated as "X-Arrestin"). In the present invention, Arrestin-2 (β-Arrestin-1) and Arrestin-3 (β-Arrestin-2) can be suitably used, and it is particularly preferable to use Arrestin-2 (β-Arrestin-1) and Arrestin-3 (β-Arrestin-2) together. When Arrestin-2 (β-Arrestin-1) and Arrestin-3 (β-Arrestin-2) are used together, signal transduction mediated by these can be both detected.

In the present invention, as the protein capable of binding to the membrane protein bound to a ligand, any of known proteins can be used, and known ones whose amino acid sequence information or genetic information are registered in public database such as NCBI and GenBank can be used. For example, as β-Arrestin-1 and β-Arrestin-2, ones derived from a human are registered respectively as NP_004032.2 and NP_004304.1, and ones derived from a mouse are registered respectively as NP:796205.1 and NP_001258287.1. These can be used in the present invention. In the present invention, for example, β-Arrestin-1 and β-Arrestin-2 represented by amino acid sequences of SEQ ID NO: 10 and SEQ ID NO: 11 can be used as the protein capable of binding to the membrane protein bound to a ligand.

In the present invention, as the "protein capable of binding to the membrane protein bound to a ligand", analogs and variants thereof can be also used as long as they can bind to the membrane protein bound to a ligand. The analogs and variants of the "protein capable of binding to the membrane protein bound to a ligand" means (a) a protein consisting of an amino acid sequence of the "protein capable of binding to the membrane protein bound to a ligand" in which 1 to 50, for example, 1 to 20, or 1 to 10 amino acids are deleted, substituted, added or inserted, and capable of binding to the membrane protein bound to a ligand, or (b) a protein consisting of an amino acid sequence having a sequence identity of 80% or more, preferably 90% or more, more preferably 95% or more, and still further preferably 99% or more with the amino acid sequence of the "protein capable of binding to the membrane protein bound to a ligand", and capable of binding to the membrane protein bound to a ligand. The sequence identify of an amino acid sequence can be calculated as described above, and may be calculated based on the entire protein capable of binding to the membrane protein bound a ligand, or may be calculated based on a binding domain capable of binding to the membrane protein bound to a ligand.

The terms "portion of these" and "portion thereof" used in relation to the protein capable of binding to the membrane protein bound to a ligand in the present invention refer to a protein consisting of an amino acid sequence of a part of the protein, and capable of binding to the membrane protein bound to a ligand. An example of such a protein includes one containing at least a part of domains, in the amino acid sequence of the protein capable of binding to the membrane protein bound to a ligand, necessary for binding to the membrane protein bound to a ligand. For example, when the protein capable of binding the membrane protein bound to a ligand is an antibody, the portion can be a partial fragment of the antibody having binding activity to the membrane protein bound to a ligand, and examples include Fab, F(ab')2, and scFV.

(1-2-2) Second Reporter Protein

In the present invention, the "second reporter protein" means a protein functioning as a reporter protein together with the first reporter protein of the first fusion protein described above. As the "second reporter protein" in the present invention, another subunit different from the first reporter protein of a split reporter protein, another fluorescent protein different from the first reporter protein in the combination of fluorescent proteins capable of causing FRET, or another protein different from the first reporter protein in the combination of a bioluminescent protein and a fluorescent protein capable of causing BRET can be used.

(1-3) Genetically Modified Non-Human Animal

In the present invention, the term "genetic modification" is used in the broadest sense, and refers to every operation performed for modifying a nucleic acid sequence of a host including introduction, into a host organism, of a gene or a gene partial sequence of a heterologous organism, and of a nucleic acid sequence having a function of a promoter or the like. In other words, the genetic modification encompasses deletion of the whole or a partial sequence of a gene of a host organism, and substitution of a gene of a host organism with a heterogenic gene having a similar function. The genetic modification further encompasses production of a nucleotide sequence encoding a fusion protein by performing amino acid substitution in a nucleotide sequence encoding a specific protein by using genetic modification technology, or performing linkage to a nucleotide sequence encoding another protein.

In the present invention, the "non-human animal" does not intend limitation, and is preferably a non-human mammal. For example, rodents such as a mouse, a rat and a hamster, non-human primates such as a monkey and a chimpanzee, other mammals such as a rabbit, a sheep, a bovine and a pig, birds, amphibians, reptiles, and fishes can be used as the non-human animal of the present invention. Rodents are particularly preferred, and a mouse is most preferred.

A genetically modified non-human animal of the present invention contains cells expressing the first fusion protein and the second fusion protein, and preferably systemically contains cells expressing the first fusion protein and the second fusion protein.

In the genetically modified non-human animal of the present invention, when a purinergic receptor ligand present in an extracellular region of a cell expressing the first fusion protein and the second fusion protein is bound to the membrane protein of the first fusion protein, the protein capable of binding to the membrane protein bound to a ligand of the second fusion protein is bound thereto. Thus, the first reporter protein of the first fusion protein and the second reporter protein of the second fusion protein are close or bound to each other, and function together as a reporter protein. By detecting the reporter protein, the position, the amount and the like of the extracellular purinergic receptor ligand in the genetically modified non-human animal of the present invention can be evaluated.

A method for detecting an extracellular purinergic receptor ligand by using the genetically modified non-human animal of the present invention will be described below.

(1-3-1) Method for Producing Genetically Modified Non-Human Animal

The genetically modified non-human animal of the present invention can be produced by a conventionally known genetic modification method, and can be produced by gene transfer of genes encoding the first fusion protein and the second fusion protein into a non-human animal. Herein, the term "gene" means a DNA, an RNA, or a DNA/RNA hybrid, and a form thereof is not especially limited as long as it encodes a prescribed protein.

The gene encoding the first fusion protein can be obtained by linking, directly or via a nucleotide sequence encoding a linker, a gene encoding the membrane protein that binds to a purinergic receptor ligand to a gene encoding the first reporter protein.

As the gene encoding the membrane protein that binds to a purinergic receptor ligand, one cloned from arbitrary gene library by using the genetic information registered in the public database may be used, or one chemically produced by gene synthesis technology may be used.

As the gene encoding the first reporter protein, a commercially available product can be used, or it may be chemically produced by gene synthesis technology together with the gene encoding the membrane protein that binds to a purinergic receptor ligand.

The gene encoding the second fusion protein can be obtained by linking, directly or via a nucleotide sequence encoding a linker, a gene encoding the protein capable of binding to the membrane protein bound to a ligand to a gene encoding the second reporter protein.

As the gene encoding the protein capable of binding to the membrane protein bound to a ligand, one cloned from arbitrary gene library by using the genetic information registered in the public database may be used, or one chemically produced by gene synthesis technology may be used.

As the gene encoding the second reporter protein, a commercially available product can be used, or it may be chemically produced by gene synthesis technology together with the gene encoding the protein capable of binding to the membrane protein bound to a ligand.

Each of the gene encoding the first fusion protein and the gene encoding the second fusion protein may include, in addition to the above-described genes, a transcription or translation regulatory sequence (such as a promoter sequence, an enhancer sequence, a splicing acceptor sequence, a terminator sequence, or a poly A sequence), a selection marker gene (such as a neomycin resistance gene, a hygromycin resistance gene, a puromycin resistance gene, a diphtheria toxin A gene, or a herpes simplex virus thymidine kinase gene), a tag sequence for isolation or purification, and the like if necessary.

A method for introducing the gene encoding the first fusion protein and the gene encoding the second fusion protein into a non-human animal is not especially limited, and can be appropriately performed by any of known methods such as a micro injection method for a DNA vector (such as a plasmid vector, a cosmid vector, or a non-plasmid vector such as bacterial artificial chromosome (BAC) or yeast artificial chromosome (YAC)) or a viral vector (such as a retroviral vector) into the pronuclei of a fertilized egg, an electroporation method for an embryonic stem cell, a sperm stem cell, an induced pluripotent stem cell (iPS cell) or the like into a cell, or a lipofection method. The gene encoding the first fusion protein and the gene encoding the second fusion protein may be incorporated into the same vector, or may be incorporated respectively into different vectors.

Besides, each of the gene encoding the first fusion protein and the gene encoding the second fusion protein may be inserted into a host chromosome. In a nonrestrictive aspect, insertion of each gene into the host chromosome can be performed through modification of an arbitrary position by random integration, or through modification of a target position by technology using a zinc finger nuclease (U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626), TALEN (U.S. Pat. Nos. 8,420,782, 8,440,431, 8,440,432, and 8,450,471) or CRISPR-Cas9 ((U.S. Pat. Nos. 8,697,359, 8,795,965, and 8,771,945). Besides, in one nonrestrictive aspect of the present invention, positions on the chromosome for inserting the gene encoding the first fusion protein and the gene encoding the second fusion protein are not especially limited, and can be, for example, Rosa 26 gene, Hippo gene, TIGRE gene or the like that are known as regions where foreign genes stably express, and the genes can be operably inserted into prescribed positions by utilizing homologous recombination or the like. Herein, the term "operably" means that the gene encoding the first fusion protein and the gene encoding the second fusion protein thus inserted can express the first fusion protein and the second fusion protein under control of a transcription regulatory sequence on the host chromosome, or under control of a transcription regulatory sequence included in each of the genes.

The genetically modified non-human animal of the present invention may be produced by introducing, into one individual (cell), both the gene encoding the first fusion protein and the gene encoding the second fusion protein, or may be produced by crossbreeding animals in which the gene encoding the first fusion protein and the gene encoding the second fusion proteins have been respectively introduced to obtain offspring animals, and selecting an offspring animal having both the gene therefrom.

The genetically modified non-human animal of the present invention is heterozygous or homozygous respectively for the gene encoding the first fusion protein and the gene encoding the second fusion protein, and is preferably homozygous for both the genes.

The genetically modified non-human animal of the present invention can be screened based on an amount of a reporter protein detected, and thus, a genetically modified non-human animal having a desired amount of the reporter protein detected can be obtained. The thus obtained genetically modified non-human animal having a desired amount of the reporter protein detected can be used in methods for evaluating and screening for a purinergic receptor ligand-dependent medicinal molecule described below.

(1-3-2) Disease Model Animal

The genetically modified non-human animal of the present invention can be a disease model animal. A "disease" is preferably a disease characterized by an extracellular purinergic receptor ligand, and examples of such a disease include cancer, acute inflammation, chronic inflammation, infectious diseases, fibrosis, physical or chemical organ lesion, and cell damage caused by an anticancer agent or the like.

In the present invention, the term "cancer" means malignant neoplasm, and may be either metastatic or nonmetastatic. For example, nonrestrictive examples of carcinoma generated from epithelial tissues of the digestive tract, the skin and the like include brain tumor, skin cancer, head and neck carcinoma, esophagus cancer, lung cancer, gastric cancer, duodenal cancer, breast cancer, prostate cancer, cervical cancer, uterine cancer, pancreatic cancer, liver cancer, colorectal cancer, colon cancer, bladder cancer, and ovarian cancer. Besides, nonrestrictive examples of sarcoma generated from non-epithelial tissues (interstice) of muscle and the like include osteosarcoma, chondrosarcoma, rhabdomyosarcoma, leiomyosarcoma, liposarcoma, and angiosarcoma. In addition, nonrestrictive examples of blood cancer derived from the hematopoietic organ include malignant lymphoma including Hodgkin's lymphoma and non-Hodgkin's lymphoma, acute myelocytic leukemia and chronic myelocytic leukemia, leukemia including acute lymphatic leukemia and chronic lymphatic leukemia, and multiple myeloma. In the present invention, the "cancer" encompasses "neoplasm". A neoplasm causes tumor formation, which is characterized partially by blood vessel formation. A neoplasm also means any pathological tissue tumor newly generated, and can be benign like, for example, angioma, glioma, or teratoma, or malignant like, for example, carcinoma, sarcoma, glioma, astrocytoma, neuroblastoma, or retinoblastoma.

The genetically modified non-human animal of the present invention can be produced as a cancer model animal having a cancer tissue. The term "cancer tissue" means a tissue containing at least one cancer cell. Accordingly, it refers to all cell types involved in formation of a tumor mass including a cancer cell and an endothelial cell, for example, in the same manner as that a cancer tissue includes a cancer cell and a blood vessel. The tumor mass means a foci of tumor tissue, and the term "tumor" means a benign neoplasm or a malignant neoplasm.

A cancer model animal can be produced by administering a carcinogen to, expressing a cancer gene through genetic modification in, and transplanting a cancer cell in the genetically modified non-human animal of the present invention based on a conventionally known method.

A disease model animal of the present invention can be used in methods for detecting a disease onset site and onset time, monitoring disease course, evaluating a medicinal molecule effective for preventing or treating the disease, evaluating toxicity and adverse reaction of a drug, and screening described below.

2. Genetically Modified Animal Cell

The present invention also relates to a genetically modified animal cell expressing a first fusion protein and a second fusion protein for detecting an extracellular purinergic receptor ligand.

In the present invention, the "first fusion protein" and the "second fusion protein" are defined in the same manner as described above.

In the present invention, the term "animal cell" means a cell derived from an animal belonging to the phylum Vertebrata or a cell derived from an invertebrate (animal excluding animals belonging to the phylum Vertebrata), and is not especially limited. The "animal cell" in the present invention preferably means a cell of an animal belonging to the phylum Vertebrata. The phylum Vertebrata includes Agnatha and Gnathostomata, and Gnathostomata includes Mammalia, Ayes, *Amphibia*, Reptilia and the like. More preferably, the "animal cell" in the present invention is a cell derived from an animal belonging to Mammalia designated as a mammal, and is not especially limited but is particularly preferably a cell derived from a mouse, a rat, a human, a monkey, a pig, a dog, a sheep, a goat or the like.

In the genetically modified animal cell of the present invention, when an extracellular purinergic receptor ligand is bound to the membrane protein of the first fusion protein, the protein capable of binding to the membrane protein bound to the ligand of the second fusion protein is bound thereto. Thus, the first reporter protein of the first fusion protein and the second reporter protein of the second fusion protein are close or bound to each other, and function together as a reporter protein. By detecting the reporter protein, the presence, the amount and the like of the extracellular purinergic receptor ligand in the genetically modified non-human animal of the present invention can be evaluated.

A method for detecting an extracellular purinergic receptor ligand by using the genetically modified animal cell of the present invention will be described below.

(2-1) Method for Producing Genetically Modified Animal Cell

The genetically modified animal cell of the present invention can be produced by a conventionally known genetic modification method, and can be produced by gene transfer of the gene encoding the first fusion protein and the gene encoding the second fusion protein into an animal cell.

The gene encoding the first fusion protein and the gene encoding the second fusion protein can be introduced into an animal cell by appropriately employing a known method, and for example, a DNA vector (such as a plasmid vector, a cosmid vector, or a non-plasmid vector such as bacterial artificial chromosome (BAC) or yeast artificial chromosome (YAC)) or a viral vector (such as a retroviral vector), an electroporation method, or a lipofection method can be used. The gene encoding the first fusion protein and the gene encoding the second fusion protein may be incorporated into the same vector, or may be incorporated respectively into different vectors.

Besides, each of the gene encoding the first fusion protein and the gene encoding the second fusion protein may be inserted into a host chromosome. In a nonrestrictive aspect, insertion of each gene into the host chromosome can be performed through modification of an arbitrary position by random integration, or through modification of a target position by technology using a zinc finger nuclease, TALEN or CRISPR-Cas9. In one nonrestrictive aspect of the present invention, positions on the chromosome for inserting the gene encoding the first fusion protein and the gene encoding the second fusion protein are not especially limited, and can be, for example, Rosa 26 gene, Hippo gene, TIGRE gene or the like, and the genes can be operably inserted into prescribed positions by utilizing homologous recombination or the like.

The genetically modified animal cell of the present invention is heterozygous or homozygous respectively for the gene encoding the first fusion protein and the gene encoding the second fusion protein, and is preferably homozygous for both the genes.

Alternatively, the genetically modified animal cell of the present invention can be produced also by isolation from the genetically modified non-human animal of the present invention described above.

The genetically modified animal cell of the present invention encompasses not only a cell used in vitro, represented by an isolated cell or a cell established as a cell line, but also a cell present in a living body. In other words, a cell contained in the living body of the genetically modified non-human animal of the present invention described above, and the genetically modified animal cell having been transplanted into a living body of an animal also correspond to the genetically modified animal cell of the present invention.

In the genetically modified animal cell of the present invention, when an extracellular purinergic receptor ligand is bound to the membrane protein that binds to a purinergic receptor ligand of the first fusion protein to activate the membrane protein, the protein that binds to the activated membrane protein of the second fusion protein is bound thereto. Thus, the first reporter protein of the first fusion protein and the second reporter protein of the second fusion protein are close or bound to each other, and function together as a reporter protein. By detecting/measuring the reporter protein, the amount of, and the presence of influence caused by the extracellular purinergic receptor ligand can be evaluated.

The genetically modified animal cell of the present invention can be included in a detection kit for detecting an extracellular purinergic receptor ligand, and thus can be provided. The kit can include, in addition to the cell, an instruction manual describing a cell culture method and a method for detecting a reporter protein, and a calibration curve indicating ranges of an amount of the reporter protein detected and an amount of an extracellular purinergic receptor ligand. The kit can further include an appropriate substrate if the reporter protein is an enzyme.

A method for detecting/evaluating an extracellular purinergic receptor ligand by using the genetically modified animal cell of the present invention will be described below.

3. Various Evaluation Methods using Genetically Modified Animal and Genetically Modified Animal Cell (3-1) Detection of Extracellular Purinergic Receptor Ligand In one aspect, the genetically modified animal and the genetically modified animal cell of the present invention can be used in a method for detecting an extracellular purinergic receptor ligand. In the present invention, the term "detecting" means qualitatively determining, and/or quantitatively measuring, and the term "detecting a purinergic receptor ligand" means either or both of qualitatively determining the presence of a purinergic receptor ligand, and quantitatively measuring an extracellular concentration of a purinergic receptor ligand.

In the present invention, detection of a purinergic receptor ligand can be performed by detecting a reporter protein. As described above, in the genetically modified animal and the genetically modified animal cell of the present invention, when an extracellular purinergic receptor ligand is bound to the membrane protein of the first fusion protein, the protein capable of binding to the membrane protein bound to the ligand of the second fusion protein is bound thereto. Thus, the first reporter protein of the first fusion protein and the second reporter protein of the second fusion protein are close or bound to each other, and function together as a reporter protein. By detecting the reporter protein, the extracellular purinergic receptor ligand can be detected.

A method for detecting a reporter protein can be appropriately selected depending on the reporter protein used, and any of general methods can be employed. For example, when a fluorescent protein is used as the reporter protein, the detection can be performed by irradiation with light of an excitation light of the fluorescent protein to detect fluorescence thus generated. Specific examples of such a fluorescent protein include GFP, CYP and YFP. Alternatively, when an enzyme is used as the reporter protein, the detection can be performed by administering or adding a substrate of the enzyme if necessary, and causing a reaction between the enzyme and the substrate to detect a reactant. If the reactant is a fluorescent substance, the detection can be performed by irradiating light of an excitation wavelength of the fluorescent substance to detect fluorescence thus generated. If the reactant emits light, the detection can be performed by measuring this light emission. Alternatively, if the reactant is a pigment, the detection can be performed by measuring the absorbance of the pigment. More specifically, when luciferase is used as the reporter protein, the detection can be performed by administering or adding cell membrane permeable luciferin as a substrate to cause a luciferin-luciferase reaction, and detecting light emission of a protein thus generated.

According to the present invention, an example of a purinergic receptor ligand includes ATP, and extracellular ATP can be detected by using the genetically modified animal and the genetically modified cell of the present invention.

(3-2) Evaluation and Screening of Medicinal Molecule

In another aspect, the genetically modified animal and the genetically modified animal cell of the present invention can be used in an evaluation method for an effect of a medicinal molecule using an extracellular purinergic receptor ligand as an index.

In this method, a test substance is administered to the genetically modified animal of the present invention, or added to a medium for culturing the genetically modified animal cell of the present invention, and if the reporter protein is an enzyme, a substrate of the enzyme is administered or added if necessary. Thus, the reporter protein is detected, the amount thereof is compared with an amount detected before the administration or addition, so that the medicinal effect of the test substance can be evaluated.

The "test substance" is not especially limited, and examples include a low molecular compound, an amino acid, a nucleic acid, a lipid, a sugar, and an extract of a natural product, and a natural compound library, a synthetic compound library, a metabolite library, an existing drug library and the like can be used.

The administration of the test substance and the substrate (if necessary) to the genetically modified animal of the present invention can be performed by arbitrary means, and can be performed by injection such as intravenous injection, intradermal injection, subcutaneous injection, intramuscular injection, or intraperitoneal injection (although not restrictive). Besides, the test substance and the substrate may be simultaneously administered to the genetically modified animal of the present invention, or separately administered, and the administration means may be the same or different.

The addition of the test substance and the substrate (if necessary) to the medium for culturing the genetically modified animal cell of the present invention may be simultaneously performed, or these may be separately added.

In the administration or the addition of the test substance, if the amount of the reporter protein detected is reduced as compared with that before the administration or the addition, the test substance can be evaluated to have an effect of suppressing production of a purinergic receptor ligand. On the other hand, if the amount of the reporter protein detected is increased as compared with that before the administration or the addition, the test substance can be evaluated to have an effect of increasing production of the purinergic receptor ligand, and furthermore, a medicinal molecule having each effect can be screened based on the evaluation.

When the test substance is cytotoxic or causes organ lesion as a principal effect or adverse effect thereof, the toxicity of the test substance can be evaluated by detecting a purinergic receptor ligand leaked from the tissue having lesion, or by detecting a purinergic receptor ligand secreted by an immune cell present in the tissue having lesion. Among these cases, if it is administered to the genetically modified animal, an organ causing toxicity can be non-invasively specified, and in addition, chronological change can be grasped.

More specifically, an example of a purinergic receptor ligand includes ATP, and in this method, ATP can be used as an index for evaluating a medicinal effect of increasing production of ATP or suppressing the production of ATP, and a medicinal molecule having such an effect can be screened.

(3-3) Evaluation and Screening of Purinergic Receptor Ligand-Dependent Medicinal Molecule In still another aspect, the genetically modified animal and the genetically modified animal cell of the present invention can be used in an evaluation method for an effect of a purinergic receptor ligand-dependent medicinal molecule.

In the present invention, the term "purinergic receptor ligand-dependent medicinal molecule" means a medicinal molecule activated or inactivated dependently on the presence or the amount of an extracellular purinergic receptor ligand.

In this method, a test substance is administered to the genetically modified animal of the present invention, or added to a medium for culturing the genetically modified animal cell of the present invention, and thus, the medicinal effect of the test substance in the presence of a prescribed amount of an extracellular purinergic receptor ligand can be evaluated.

In this method, the amount of an extracellular purinergic receptor ligand in the genetically modified animal of the present invention, or the genetically modified animal cell of the present invention can be confirmed by detecting a reporter protein. The detection of a reporter protein may be performed so that the amount of an extracellular purinergic receptor ligand at least when the test substance is effective can be revealed, and can be performed either or both before the administration or the addition of the test substance, and after the administration or the addition. Preferably, the detection of a reporter protein can be performed before the administration or the addition of the test substance.

In this method, the genetically modified animal of the present invention having been precedently screened based on an amount of a prescribed reporter protein detected can be used.

Alternatively, the amount of an extracellular purinergic receptor ligand in the genetically modified animal of the present invention, or the genetically modified animal cell of the present invention may be adjusted by administering the purinergic receptor ligand to the genetically modified animal of the present invention, or by adding it to a medium for culturing the genetically modified animal cell of the present invention.

The "test substance" has been described above, and the administration or the addition of the test substance and a substrate (if necessary) can be performed by arbitrary means as described above.

The detection of a reporter protein can be performed as described above in accordance with the reporter protein used.

When the medicinal effect is found to be changed dependently on the presence or the amount of an extracellular purinergic receptor ligand, the test substance can be evaluated as a purinergic receptor ligand-dependent medicinal molecule, and the purinergic receptor ligand-dependent medicinal molecule can be screened based on the evaluation.

More specifically, an example of a purinergic receptor ligand includes ATP, and in this method, the effect of an ATP-dependent medicinal molecule can be evaluated, and the ATP-dependent medicinal molecule can be screened.

(3-4) Screening of Medicinal Molecule for Monitoring Disease Condition, and Preventing or Treating Disease In still another aspect, the genetically modified animal of the present invention can be used in a method for detecting an onset site and an onset time of a disease, or for monitoring a disease condition. In this method, by detecting a reporter protein in the disease model animal described above, the onset site or degree, and the onset time of a disease characterized by an extracellular purinergic receptor ligand can be specified, and when these are specified chronologically, the course of the disease condition can be monitored.

Besides, in still another aspect, the genetically modified animal of the present invention can be used in a method for evaluating a preventive agent or a therapeutic agent for a disease, or screening for an effective preventive agent or therapeutic agent.

In this method, a test substance is administered to the disease model animal described above, and if the reporter protein is an enzyme, a substrate of the enzyme is further administered, and the reporter protein is detected to compare the amount detected with an amount detected before the administration, and thus, the medicinal effect of the test substance can be evaluated.

In the administration of the test substance, if the amount of the reporter protein detected is reduced as compared with that before the administration, the test substance can be evaluated as effective for preventing or treating the disease, and a medicinal molecular having each effect can be screened based on the evaluation.

The "test substance" has been described above, and the administration of the test substance and a substrate (if necessary) can be performed by arbitrary means as described above.

The detection of a reporter protein can be performed as described above in accordance with the reporter protein used.

More specifically, an example of a purinergic receptor ligand includes ATP, and in this method, ATP can be used as an index for evaluating an effect of a medicinal molecule effective for prevention or treatment of cancer, and a medicinal molecule effective for prevention or treatment of cancer can be screened. Besides, in this method, a medicinal molecule effective for prevention or treatment of another disease different from cancer, or an adverse effect of another agent can be screened. Nonrestrictive examples of another disease different from cancer or the adverse effect include acute inflammation, chronic inflammation, infectious disease, fibrosis, physical or chemical organ lesion, and cell damage caused by an anticancer agent or the like, and the effect of a medicinal molecule effective for prevention or treatment of these diseases or adverse effect can be evaluated with ATP used as an index.

It is noted that terms herein used should not be interpreted as being limited in number unless the terms are described with limitation in number such as "one" or "plural", but should be understood to have meaning of "one or plural".

Those skilled in the art will naturally understand that the present invention encompasses an arbitrary combination of one or a plurality of aspects herein described unless it is technically contradictory based on common technical knowledge of those skilled in the art.

All the related art literatures cited herein are incorporated herein by reference.

This application encompasses contents of the specification and/or drawings of Japanese Patent Application No. 2019-225404, based on which this application claims the benefit of priority.

EXAMPLES

Next, the present invention will be more specifically described by way of examples, and it is noted that the present invention is not limited to the following examples.

[Example 1] Production of P2Y11-Split Luc (C-Terminal)/Arrestin-Split Luc (N-Terminal) Double Knock-In Mouse 1.1. Construction of P2Y11-Split Luc (C-Terminal) Knock-In Vector A splicing acceptor, a poly A addition signal, and a FLAG tag were added to a sequence obtained by binding human P2Y11 gene and a C-terminal side region of Luciferase gene to obtain "P2Y11-split Luc (C-terminal)" expression cassette (SEQ ID NO: 1). The resultant sequence was cloned into a homologous recombination vector, pZDonor-mRosa26 vector (SIGMA-Aldric Inc., #D9196), for knock-in in a mouse Rosa gene region by a method known to those skilled in the art, and thus, a P2Y11-split Luc (C-terminal) knock-in vector was constructed (FIG. 1).

1.2. Construction of Arrestin-Split Luc (N-Terminal) Knock-In Vector

A Myc tag and a His tag were respectively added to a sequence obtained by binding mouse Arrestin-2 (β-Arrestin-1) gene (illustrated as "mArrb1a" in FIG. 2) and an N-terminal side region of Luciferase gene, and a sequence obtained by binding mouse Arrestin-3 (β-Arrestin-2) gene (illustrated as "mArrb2a" in FIG. 2) and the N-terminal side region of Luciferase gene, so as to be linked via a 2A peptide, and the resultant was combined with a mouse β actin promoter to obtain "Arrestin-split Luc (N-terminal)" expression cassette (SEQ ID NO: 2). The resultant sequence was cloned into a homologous recombination vector, pZDonor-mRosa26 vector (SIGMA-Aldric Inc., #D9196), for knock-in in a mouse Rosa gene region by a method known to those skilled in the art, and thus, Arrestin-split Luc (N-terminal) knock-in vector was constructed (FIG. 2).

1.3. DNA Microinjection of P2Y11-Split Luc (C-Terminal) and Arrestin-Split Luc (N-Terminal) Knock-In Vectors into Mouse Fertilized Eggs A solution obtained by mixing each of the P2Y11-split Luc (C-terminal) knock-in vector or the Arrestin-split Luc (N-terminal) knock-in vector with ZFN mRNA (SIGMA-Aldric Inc., #M4574) targeting mouse Rosa gene was injected respectively into the pronuclei of a mouse fertilized egg. The embryo after the injection was cultured at 37° C. overnight, and the embryo having developed to the two cell stage was transplanted into the uterus of an ICR receptive female mouse of 0.5 days false pregnancy to obtain an offspring. The thus obtained offspring were detected for the knock-in allele by PCR to select a founder mouse. For the knock-in allele detection in a P2Y11-split Luc (C-terminal) knock-in mouse, primers: mR1387F (SEQ ID NO: 3) and h11-480R (SEQ ID NO: 4), and FLucC-1321F (SEQ ID NO: 5) and mR3334R (SEQ ID NO: 6) were used, and for the knock-in allele detection in an Arrestin-split Luc (N-terminal) knock-in mouse, primers: mR1247Fq (SEQ ID NO: 3) and cmv-R (SEQ ID NO: 7), and mArrb2a-F2 (SEQ ID NO: 8) and mR3334R (SEQ ID NO: 6) were used.

1.4. Production of P2Y11-Split Luc (C-Terminal)/Arrestin-Split Luc (N-Terminal) Double Knock-In Mouse The founder mouse thus obtained was crossbred with a C57BL/6N mouse after sexual maturity, and PCR was performed with a genomic DNA extracted from a next generation mouse used as a template to confirm transmission of the knock-in allele to the next generation mouse. The P2Y11-split Luc (C-terminal) knock-in mouse and the Arrestin-split Luc (N-terminal) knock-in mouse thus respectively established were intercrossed to produce a P2Y11-split Luc (C-terminal)/Arrestin-split Luc (N-terminal) double knock-in mouse.

[Example 2] Detection of In Vivo ATP Signal in P2Y11-Split Luc (C-Terminal)/Arrestin-Split Luc (N-Terminal) Double Knock-In Mouse To a P2Y11-split Luc (C-terminal)/Arrestin-split Luc (N-terminal) double knock-in mouse, 50 μL of a mixture of ATP at a final concentration of 1 mM and 15 mg/mL VivoGlo Luciferin (Promega #P1043) was subcutaneously administered. A luminescent signal intensity was measured with IVIS Spectrum CT (Perkin Elmer) 10 to 20 minutes after the ATP administration. The measurement was performed under conditions of exposure time of 180 sec, with medium binning, and F/stop of 1, and thus the luminescent signal was analyzed in terms of a physical quantity (photons/sec).

As a result, a luminescent signal due to the ATP administration was detected in the P2Y11-split Luc (C-terminal)/Arrestin-split Luc (N-terminal) double knock-in mouse, and this luminescent signal was detected neither in a mouse having merely one of the alleles nor in a wild type mouse (FIG. 3). It was confirmed from this result that when ATP is bound to P2Y11, Arrestin is recruited to reconstruct split-Luciferase, and the resultant functions as a reaction specific reporter mouse capable of providing a luminescent signal.

[Example 3] Establishment of Fibroblast Derived from P2Y11-Split Luc (C-Terminal)/Arrestin-Split Luc (N-Terminal) Double Knock-In Mouse, and Detection of In Vitro ATP Signal 3.1. Establishment of Fibroblast Derived from P2Y11-Split Luc (C-Terminal)/Arrestin-Split Luc (N-Terminal) Double Knock-In Mouse A skin tissue was collected from a P2Y11-split Luc (C-terminal)/Arrestin-split Luc (N-terminal) double knock-in mouse, and was sliced with a scalpel in a culture fluid, and the resultant was covered with a cover glass with a dermis side in contact with a bottom of a culture dish, and was cultured in a D-MEM medium supplemented with 10% FBS and 1×NEAA. Fibroblasts confirmed to have migration/growth of cells were collected by a trypsin treatment, and the resultant was repeatedly passaged to establish a fibroblast cell line.

3.2. Detection of In Vitro ATP Concentration

The fibroblast derived from the P2Y-11 split Luc (C-terminal)/Arrestin-split Luc (N-terminal) double knock-in mouse was seeded in a 24-well culture plate. On the next day, ATP at a final concentration of 0 to 1000 μM and VivoGlo Luciferin (Promega #P1043) were added thereto, and a luminescent signal was detected with IVIS Spectrum CT (Perkin Elmer). The measurement was performed under conditions of exposure time of 180 sec, with medium binning, and F/Stop of 1, and thus the luminescent signal was analyzed in terms of a physical quantity (photons/sec).

As a result, a concentration-dependent signal intensity was detected in using 0 μM, 10 μM, 50 μM, 100 μM, 200 μM, 400 μM, 600 μM, 800 μM, and 1000 μM ATP, and a regression equation of $y=437.91x+10840$ ($R^2=0.9727$) was obtained (FIG. 4 and FIG. 5).

[Example 4] In Vivo Imaging of ATP at Known Concentration

To a P2Y11-split Luc (C-terminal)/Arrestin-split Luc (N-terminal) double knock-in mouse, 50 μL of a mixture of ATP at a final concentration of 0 mM, 1 mM, 2 mM, 4 mM, or 8 mM and 15 mg/mL VivoGlo Luciferin (Promega #P1043) was subcutaneously administered. A luminescent signal intensity was measured with IVIS Spectrum CT (Perkin Elmer) 10 to 20 minutes after the ATP administration. The measurement was performed under conditions of exposure time of 60 sec, with medium binning, and F/stop of 1, and thus the luminescent signal was analyzed in terms of a physical quantity (photons/sec). As a result, an ATP concentration-dependent signal intensity was detected, and a regression equation of $y=1E+06x+3E+06$ ($R^2=0.9964$) was obtained. Thus it was confirmed that the mouse functions as a concentration dependent reporter mouse (FIG. 6 and FIG. 7).

[Example 5] Visualization of ATP by Inflammatory Stimulus

A P2Y11-split Luc (C-terminal)/Arrestin-split Luc (N-terminal) double knock-in mouse was subjected to hydrodynamic injection to make examination on visualization of ATP leakage in the liver caused through liver cell damage. After the next day of the hydrodynamic injection through the tail vein of saline in an amount corresponding to 10% of the weight of the mouse, 150 mg/kg of VivoGlo Luciferin (Promega #P1043) was intraperitoneally administered, and a luminescent signal intensity was measured with IVIS Spectrum CT (Perkin Elmer). The measurement was performed under conditions of exposure time of 60 sec, with medium binning, and F/Stop of 1, and thus the luminescent signal was analyzed in terms of a physical quantity (photons/sec).

As a result, a high luminescent signal was detected in the liver of a hydrodynamic injection group as compared with a group (-) not subjected to the hydrodynamic injection, and thus, it was confirmed that the mouse can be a reporter mouse in which ATP leakage through inflammatory stimulus is non-invasively visualized (FIG. 8).

[Example 6] Visualization of Interstitial ATP Through Carcinogenesis Induction

In a P2Y11-split Luc (C-terminal)/Arrestin-split Luc (N-terminal) double knock-in mouse, examination was made on carcinogenesis induction in the liver by hydrodynamic DNA delivery, comparison in the ATP concentration between a normal tissue and a tumor mass formation site, and visualization thereof. Specifically, saline was mixed with a mutant Kras expression vector and gRNA-Cas9 expression vectors targeting p53, p16 and Smad4 genes, each vector in an amount of 3 to 5 μg/mouse, and the resultant was administered into the tail vein in an amount corresponding to about 10% of the weight of the mouse. Mutant Kras expression was performed using an expression vector pMacII used in The Journal of Biological Chemistry (2011) 286, 20109-20116. A sequence encoding mutant Kras (G12D) shown in SEQ ID NO: 12 was cloned into the expression vector pMacII for use. In this construction, the mutant Kras (G12D) was expressed under control of a CMV enhancer and a mouse beta actin promoter. For each of the gRNA-Cas9 expression vectors targeting the respective target genes, a partial sequence of the p53, the p16 or the Smad4 genes was used as a gRNA sequence to be cloned into pGENA22 (Horizon Discovery Ltd.). Three gRNA-Cas9 expression vectors were created for each of the target genes, and these three vectors were mixed for the administration. As the gRNA sequences for p53, sequences respectively shown in SEQ ID NOS: 13, 14 and 15 were used. As the gRNA sequences for p16, sequences respectively shown in SEQ ID NOS: 16, 17 and 18 were used. As the gRNA sequences for Smad4, sequences respectively shown in SEQ ID NOS: 19, 20 and 21 were used. For analysis of a change in the concentration of interstitial ATP through carcinogenesis in the liver, 150 mg/kg VivoGlo Luciferin (Promega #P1043) was intraperitoneally administered, and a luminescent signal intensity was measured with IVIS Spectrum CT (Perkin Elmer). The measurement was performed under conditions of exposure time of 120 sec (in vivo) or 1 sec (excised liver), with medium binning, and F/Stop of 1, and thus the luminescent signal was analyzed in terms of a physical quantity (photons/sec).

As a result, in an individual in which formation and increase of a tumor mass in the liver were found as a result of the administration of the mutant Kras expression vector and the gRNA-Cas9 expression vectors targeting the p53, p16 and Smad4 genes, a strong luminescent signal was detected through non-invasive visualization (FIG. 9(A)). Furthermore, the liver was excised for comparing, through ex vivo analysis, with a normal tissue or a normal region, and a high luminescent signal was detected in a region found to be cancerated and a tumor mass formation site, and it was thus confirmed that the ATP concentration is high in a cancer cell growth region (FIG. 9(B)).

The invention claimed is:

1. A genetically modified non-human animal expressing a first fusion protein and a second fusion protein for detecting extracellular ATP, wherein the first fusion protein comprises (a) a membrane protein that comprises P2Y11 or a portion thereof that comprises a transmembrane domain and binds to ATP, and (b) a first reporter protein;

the second fusion protein comprises (i) an Arrestin or a portion thereof that binds to the membrane protein bound to ATP, and (ii) a second reporter protein; and the first reporter protein and the second reporter protein are intracellularly located and are respective subunits of a split reporter protein.

2. The genetically modified non-human animal according to claim 1, wherein the split reporter protein is split luciferase.

3. The genetically modified non-human animal of claim 1, wherein the first fusion protein comprises P2Y11.

4. The genetically modified non-human animal of claim 1, wherein the first fusion protein comprises a portion of P2Y11 comprising a transmembrane domain and a domain that binds to extracellular ATP, provided that the first fusion protein does not comprise all of P2Y11.

5. The genetically modified non-human animal of claim 1, wherein the second fusion protein comprises an Arrestin.

6. The genetically modified non-human animal of claim 1, wherein the second fusion protein comprises a portion of an Arrestin comprising a domain that binds to the membrane protein bound to ATP, provided that the second fusion protein does not comprise all of the Arrestin.

7. The genetically modified non-human animal of claim 1, wherein the Arrestin is β-Arrestin-1 or β-Arrestin-2.

8. The genetically modified non-human animal of claim 1, wherein the second fusion protein comprises β-Arrestin-1 or β-Arrestin-2.

9. The genetically modified non-human animal of claim 1, wherein the second fusion protein comprises both β-Arrestin-1 and β-Arrestin-2.

10. An animal cell expressing a first fusion protein and a second fusion protein for detecting extracellular ATP, wherein the first fusion protein comprises (a) a membrane protein that comprises P2Y11or a portion thereof that comprises a transmembrane domain and binds to extracellular ATP, and (b) a first reporter protein;

the second fusion protein comprises (i) an Arrestin or a portion thereof that binds to the membrane protein bound to ATP and (ii) a second reporter protein; and the first reporter protein and the second reporter protein are intracellularly located and are respective subunits of a split reporter protein.

11. The animal cell according to claim 10, wherein the split reporter protein is split luciferase.

12. The animal cell of claim 10, wherein the first fusion protein comprises P2Y11.

13. The animal cell of claim 10, wherein the first fusion protein comprises a portion of P2Y11 comprising a transmembrane domain and a domain that binds to extracellular ATP, provided that the first fusion protein does not comprise all of P2Y11.

14. The animal cell of claim 10, wherein the second fusion protein comprises an Arrestin.

15. The animal cell of claim 10, wherein the second fusion protein comprises a portion of an Arrestin comprising a domain that binds to the membrane protein bound to ATP, provided that the second fusion protein does not comprise all of the Arrestin.

16. The animal cell of claim 10, wherein the Arrestin is β-Arrestin-1 or β-Arrestin-2.

17. The animal cell of claim 10, wherein the second fusion protein comprises β-Arrestin-1 or β-Arrestin-2.

18. The animal cell of claim 10, wherein the second fusion protein comprises both β-Arrestin-1 and β-Arrestin-2.

* * * * *

SEQUENCE LISTING

```
<160> NUMBER OF SEQ ID NOS: 21

<210> SEQ ID NO 1
<211> LENGTH: 1827
<212> TYPE: DNA
<213> ORGANISM: Artificial Sequence
<220> FEATURE:
<223> OTHER INFORMATION: splicing acceptor (human
      Adenovirus)-hP2Y11-linker-splitFLuc(C)-FLAG-timidine kinase polyA

<400> SEQUENCE: 1

aagggcgcag tagtccaggg tttccttgat gatgtcatac ttatcctgtc ccttttttt      60

ccacagccgg ccaccatggc agccaacgtc tcgggtgcca agtcctgccc tgccaacttc    120

ttggcagctg ccgacgacaa actcagtggg ttccaggggg acttcctgtg gcccatactg    180

gtggttgagt tcctggtggc cgtggccagc aatggcctgg ccctgtaccg cttcagcatc    240

cggaagcagc gcccatggca ccccgccgtg gtcttctctg tccagctggc agtcagcgac    300

ctgctctgcg ccctgacgct gcccccgctg gccgcctacc tctatccccc caagcactgg    360

cgctatgggg aggccgcgtg ccgcctggag cgcttcctct tcacctgcaa cctgctgggc    420

agcgtcatct tcatcacctg catcagcctc aaccgctacc tgggcatcgt gcaccccttc    480

ttcgcccgaa gccacctgcg acccaagcac gcctgggccg tgagcgctgc cggctgggtc    540

ctggccgccc tgctggccat gcccacactc agcttctccc acctgaagag gccgcagcag    600

ggggcgggca actgcagcgt ggccaggccc gaggcctgca tcaagtgtct ggggacagca    660

gaccacgggc tggcggccta cagagcgtat agcctggtgc tggcggggtt gggctgcggc    720

ctgccgctgc tgctcacgct ggcagcctac ggcgccctcg ggcgggccgt gctacgcagc    780

ccaggcatga ctgtggccga gaagctgcgt gtggcagcgt tggtggccag tggtgtggcc    840

ctctacgcca gctcctatgt gccctaccac atcatgcggg tgctcaacgt ggatgctcgg    900

cggcgctgga gcacccgctg cccgagcttt gcagacatag cccaggccac agcagccctg    960

gagctggggc cctacgtggg ctaccaggtg atgcggggcc tcatgcccct ggccttctgt   1020

gtccaccctc tactctacat ggccgcagtg cccagcctgg gctgctgctg ccgacactgc   1080

cccggctaca gggacagctg gaacccagag gacgccaaga gcactggcca agccctgccc   1140

ctcaatgcca cagccgcccc taaaccgtca gagccccagt cccgtgagct gagccaaggc   1200

tcgagtggag gtggcggttc tggtggtggg ggcagtggcg gtggaggtag tggaggcggc   1260

ggaatgagcg gctacgttaa caaccccgag gctacaaacg ctctcatcga caaggacggc   1320

tggctgcaca gcggcgacat cgcctactgg gacgaggacg agcacttctt catcgtggac   1380
```

```
cggctgaaga gcctgatcaa atacaagggc taccaggtag ccccagccga actggagagc   1440

atcctgctgc aacaccccaa catcttcgac gccggggtcg ccggcctgcc cgacgacgat   1500

gccggcgagc tgcccgccgc agtcgtcgtg ctggaacacg gtaaaaccat gaccgagaag   1560

gagatcgtgg actatgtggc cagccaggtt acaaccgcca agaagctgcg cggtggtgtt   1620

gtgttcgtgg acgaggtgcc taaaggactg accggcaagt tggacgcccg caagatccgc   1680

gagattctca ttaaggccaa gaagggcggc aagatcgccg tgggcccgcg gttcgaagac   1740

tacaaggacg acgatgacaa gtgataaacg cgtggcaata aaaagacaga ataaaacgca   1800

cgggtgttgg gtcgtttgtt cgctagc                                       1827


<210> SEQ ID NO 2
<211> LENGTH: 8656
<212> TYPE: DNA
<213> ORGANISM: Artificial Sequence
<220> FEATURE:
<223> OTHER INFORMATION: Enhancer sequence (CMV)-beta actin promoter-
      beta globin exon_intron-splitFLuc(N)-mArrb1a-MycTag--GSG
      linker-2A-splitFLuc(N)-mArrb2a-HisTag-beta globin polyA

<400> SEQUENCE: 2

attgattatt gactagttat taatagtaat caattacggg gtcattagtt catagcccat     60

atatggagtt ccgcgttaca taacttacgg taaatggccc gcctggctga ccgcccaacg    120

acccccgccc attgacgtca ataatgacgt atgttcccat agtaacgcca atagggactt    180

tccattgacg tcaatgggtg gagtatttac ggtaaactgc ccacttggca gtacatcaag    240

tgtatcatat gccaagtacg ccccctattg acgtcaatga cggtaaatgg cccgcctggc    300

attatgccca gtacatgacc ttatgggact ttcctacttg gcagtacatc tacgtattag    360

tcatcgctat taccatggtg gatctgggag tgactctctg tccattcaat ccaggccccg    420

cgtgtccctc aaacaagagg ccacacaaat agggtccggg cctcgatgct gaccctcatc    480

cacttaagtg ctcgatatcc acgtgacatc cacacccaga gggtcctggg gtggttgggt    540

gacccccaga atgcaggcct agtaaccgag acattgaatg gggcagtgtc cacaagggcg    600

gaggctattc ctgtacatct gggcctacgg agccagcacc catcgccaaa actcttcatc    660

ctcttcctca atctcgcttt ctctctcgct tttttttttt ttcttcttct tttttttttt    720

ttttttcaaa aggaggggag agggggtaaa aaaatgctgc actgtgcggc gaggccggtg    780

agtgagcgac gcggagccaa tcagcgcccg ccgttccgaa agttgccttt tatggctcga    840

gtggccgctg tggcgtccta taaaacccgg cggcgcaacg cgcagccact gtcgagtcgc    900

gtccacccgc gagcacagct tctttgcagc tccttcgttg ccggtccaca cccgccacca    960

ggtaagcagg gacgccgggc ccagcgggcc ttcgctctct cgtggctagt acctcactgc   1020

agggtcctga ggatcactca gaacggacac catgggcggg tggagggtgg tgccgggccg   1080

cggagcggac actggcacag ccaactttac gcctagcgtg tagactcttt gcagccacat   1140

tcccgcggtg tagacactcg tgggcccgct cccgctcggt gcgtggggct tggggacaca   1200

ctagggtcgc ggtgtgggca tttgatgagc cggtgcggct tgcgggtgtt aaaagccgta   1260

ttaggtccat cttgagagta cacagtattg ggaaccagac gctacgatca cgcctcaatg   1320

gcctctgggt ctttgtccaa accggtttgc ctattcggct tgccgggcgg gcgggcgggc   1380

gggcgggcgc ggcagggccg gctcggccgg gtgggggctg ggatgccact gcgcgtgcgc   1440

tctctatcac tgggcatcga ggcgcgtgtg cgctagggag ggagctcttc ctctccccct   1500

cttcctagtt agctgcgcgt gcgtattgag gctgggagcg cggctgcccg ggttgggcg    1560
```

```
agggcggggc cgttgtccgg aaggggcggg gtcacagtgg cacgggcgcc ttgtttgcgc   1620
ttcctgctgg gtgtggtcgc ctcccgcgcg cgcacaagcc gcccgtcggc gcagtgtagg   1680
cggagcttgc gcccgtttgg ggagggggcg gaggtctggc ttcctgccct aggtccgcct   1740
ccgggccagc gtttgccttt tatggtaata atgcggccgg tctgcgcttc ctttgtcccc   1800
tgagcttggg cgcgcgcccc ctggcggctc gagcccgcgg cttgccggaa gtgggcaggg   1860
cggcagcggc tgctcttggc ggccccgagg tgactatagc cttcttttgt gtcttgatag   1920
ttcgccaagc tggatcctga gaacttcagg gtgagtctga tgggcacctc ctgggtttcc   1980
ttcccctggc tattctgctc aaccttccta tcagaaggaa aggggaagcg attctaggga   2040
gcagtctcca tgactgtgtg tggagtgttg acaagagttt ggatatttta ttctctactc   2100
agaatcgctg ctccccctca ctctgttctg tgttgtcatt tcctctttct ttggtaagct   2160
tttaatttcc agttgcattt tactaaatta attaagctgg ttatttactt cccatcctga   2220
tatcagcttc ccctcctcct ttcctcccag tccttctctc tctcctctct ctttctctaa   2280
tcctttcctt tccctcagtt catttcttct tctttgatct acttttgttt gtctttttaa   2340
atattgcctt gtaacttact cagaggacaa ggaagatatg tccctgtttc ttctcatagc   2400
tctcaagaat agtagcataa ttggctttta tgccagggtg acaggggaag aatatatttt   2460
acatataaat tctgtttgac ataggattct tataataatt tgtcagcagt ttaaggttgc   2520
aaacaaatgt ctttataaat aagcctgcag tatctggtat ttttgctcta cagttatgtt   2580
gatggttctt ccatattccc acagctcctg ggcaatcgga attcgccacc atggaagatg   2640
ccaaaaacat taagaagggc ccagcgccat tctacccact cgaagacggg accgccggcg   2700
agcagctgca caaagccatg aagcgctacg ccctggtgcc cggcaccatc gcctttaccg   2760
acgcacatat cgaggtggac attacctacg ccgagtactt cgagatgagc gttcggctgg   2820
cagaagctat gaagcgctat gggctgaata caaaccatcg gatcgtggtg tgcagcgaga   2880
atagcttgca gttcttcatg cccgtgttgg gtgccctgtt catcggtgtg gctgtggccc   2940
cagctaacga catctacaac gagcgcgagc tgctgaacag catgggcatc agccagccca   3000
ccgtcgtatt cgtgagcaag aaagggctgc aaaagatcct caacgtgcaa aagaagctac   3060
cgatcataca aaagatcatc atcatggata gcaagaccga ctaccagggc ttccaaagca   3120
tgtacacctt cgtgacttcc catttgccac ccggcttcaa cgagtacgac ttcgtgcccg   3180
agagcttcga ccgggacaaa accatcgccc tgatcatgaa cagtagtggc agtaccggat   3240
tgcccaaggg cgtagcccta ccgcaccgca ccgcttgtgt ccgattcagt catgcccgcg   3300
accccatctt cggcaaccag atcatccccg acaccgctat cctcagcgtg gtgccatttc   3360
accacggctt cggcatgttc accacgctgg gctacttgat ctgcggcttt cgggtcgtgc   3420
tcatgtaccg cttcgaggag gagctattct tgcgcagctt gcaagactat aagattcaat   3480
ctgccctgct ggtgcccaca ctatttagct tcttcgctaa gagcactctc atcgacaagt   3540
acgacctaag caacttgcac gagatcgcca gcggcggggc gccgctcagc aaggaggtag   3600
gtgaggccgt ggccaaacgc ttccacctac caggcatccg ccagggctac ggcctgacag   3660
aaacaaccag cgccattctg atcacccccg aaggggacga caagcctggc gcagtaggca   3720
aggtggtgcc cttcttcgag gctaaggtgg tggacttgga caccggtaag acactgggtg   3780
tgaaccagcg cggcgagctg tgcgtccgtg gccccatgat catgagcggc tacgttaaca   3840
accccgaggc tacaaacgct ctcatcgaca aggacggcgg aggaggcgga gatatcatgg   3900
```

gcgacaaagg gacacgagtg ttcaagaagg caagccccaa tggaaagctc actgtctacc 3960
tgggaaagcg ggactttgtg gaccacattg acctcgtgga ccccgtggat ggtgtggtcc 4020
tggtggatcc tgagtatctc aaagaaaggc gagtctacgt gacactgacc tgcgccttcc 4080
ggtatggccg ggaagacctg gatgtcttgg gtctgacttt tcggaaagac ctgtttgtgg 4140
ccaatgtgca gtccttccca ccggcccccg aggacaagaa gccactgaca cggctacagg 4200
agcgactcat caagaagctg ggcgagcatg cctgcccctt cacctttgag atcccgccaa 4260
accttccatg ctcagtcact ctgcagcctg ggcctgagga cacaggaaag gcctgtggtg 4320
tggattatga agtcaaagcc ttctgtgctg agaacctgga ggagaagatc cacaaaagga 4380
actctgtgcg gctagtcatc cggaaggttc agtatgcccc tgagagacct ggccctcagc 4440
ccacggctga gactaccaga cagttcctta tgtcagacaa gcccctacac cttgaggcat 4500
cactggataa ggagatctat taccacggag aacccatcag cgttaatgtc cacgtcacca 4560
acaacaccaa caagactgtg aagaagatca agatctcggt gcgccagtat gcagacatct 4620
gtctcttcaa cacagctcag tacaagtgcc cagtggccat ggaggaggct gatgacaatg 4680
tggcacccag ctcaacattc tgcaaggtct atacgctgac tcccttcctg gccaacaacc 4740
gagagaagcg gggactcgcc ctcgacggga agctcaagca tgaggacacg aatctggctt 4800
ccagcacgct gttgcgggaa ggtgccaacc gtgaaatcct gggcatcatc gtttcctaca 4860
aagtcaaggt gaaactggtg gtgtcccggg gcggcctctt gggagacctt gcatccagtg 4920
atgtggccgt ggagctgcct tttaccctaa tgcaccccaa gcctaaggag gagcccccac 4980
atcgggaagt tccagagagc gagactccag tagacaccaa tctcatagag cttgacacca 5040
atgatgacga cattgtattt gaggactttg ctcgccagcg gctgaaaggc atgaaggatg 5100
acaaggacga agaggatgac ggcaccggct ctccgcacct caacaacaga gaacaaaaac 5160
tcatctcaga agaggatctg tctagaggaa gcggagctac taacttcagc ctgctgaagc 5220
aggctggaga cgtggaggag aaccctggac ctatggaaga tgccaaaaac attaagaagg 5280
gcccagcgcc attctaccca ctcgaagacg ggaccgccgg cgagcagctg cacaaagcca 5340
tgaagcgcta cgccctggtg cccggcacca tcgcctttac cgacgcacat atcgaggtgg 5400
acattaccta cgccgagtac ttcgagatga gcgttcggct ggcagaagct atgaagcgct 5460
atgggctgaa tacaaaccat cggatcgtgg tgtgcagcga gaatagcttg cagttcttca 5520
tgcccgtgtt gggtgccctg ttcatcggtg tggctgtggc cccagctaac gacatctaca 5580
acgagcgcga gctgctgaac agcatgggca tcagccagcc caccgtcgta ttcgtgagca 5640
agaaagggct gcaaaagatc ctcaacgtgc aaaagaagct accgatcata caaaagatca 5700
tcatcatgga tagcaagacc gactaccagg gcttccaaag catgtacacc ttcgtgactt 5760
cccatttgcc acccggcttc aacgagtacg acttcgtgcc cgagagcttc gaccgggaca 5820
aaaccatcgc cctgatcatg aacagtagtg gcagtaccgg attgcccaag ggcgtagccc 5880
taccgcaccg caccgcttgt gtccgattca gtcatgcccg cgaccccatc ttcggcaacc 5940
agatcatccc cgacaccgct atcctcagcg tggtgccatt tcaccacggc ttcggcatgt 6000
tcaccacgct gggctacttg atctgcggct ttcgggtcgt gctcatgtac cgcttcgagg 6060
aggagctatt cttgcgcagc ttgcaagact ataagattca atctgccctg ctggtgccca 6120
cactatttag cttcttcgct aagagcactc tcatcgacaa gtacgaccta agcaacttgc 6180
acgagatcgc cagcggcggg gcgccgctca gcaaggaggt aggtgaggcc gtggccaaac 6240
gcttccacct accaggcatc cgccagggct acggcctgac agaaacaacc agcgccattc 6300

```
tgatcacccc cgaaggggac gacaagcctg gcgcagtagg caaggtggtg cccttcttcg   6360
aggctaaggt ggtggacttg gacaccggta agacactggg tgtgaaccag cgcggcgagc   6420
tgtgcgtccg tggccccatg atcatgagcg gctacgttaa caaccccgag gctacaaacg   6480
ctctcatcga caaggacggc ggaggaggcg gagatatcat gggagaaaaa cccgggacca   6540
gggtcttcaa gaagtcgagc cctaactgca agctcaccgt gtacttgggc aagcgcgact   6600
ttgtagatca cctggacaaa gtggaccctg tggatggcgt ggtgcttgtg gatcctgact   6660
acttgaagga ccggaaagtg ttcgtgaccc tcacctgtgc cttccgctat ggccgagaag   6720
acctggatgt actgggcctg tctttccgca aagatctgtt catcgccacc taccaggcct   6780
tcccccccat gcccaaccca cctcggcccc ccacccgcct acaggaccga ctgctgaaga   6840
agttgggcca acacgcccac cccttctttt tcacgatacc ccaaaatttg ccttgctccg   6900
tcacactgca gccaggacca gaggacacag ggaaggcttg tggagtagac tttgagattc   6960
gagctttctg tgccaaatca atagaagaaa aaagtcacaa gaggaactct gtgcggctta   7020
tcatcagaaa ggtacagttt gctcctgaga cacccggtcc ccagccctca gctgaaacca   7080
cacgccactt cctcatgtct gaccggaggt ccctccacct agaggcttcc ctggacaaag   7140
agctgtacta ccacggggag ccccttaatg tcaacgtcca tgtcaccaac aattctgcca   7200
agaccgtcaa gaagatcaga gtgtctgtga gacagtacgc cgacatttgc ctcttcagca   7260
ccgcgcagta caagtgtccc gtggctcagc tagaacaaga tgaccaggtg tctcctagtt   7320
ccacgttctg caaggtgtac accatcaccc cgctgctcag tgacaaccga gagaagcgtg   7380
gccttgcctt ggatgggcag ctcaaacatg aagacaccaa cctggcttcc agcaccattg   7440
tgaaggaggg agccaacaag gaggtgctgg ggatcctggt atcctacagg gtcaaggtga   7500
agctggtggt gtctcgaggc ggagatgtct ccgtggagct acccttcgtc ctaatgcacc   7560
ccaagcccca tgaccacatc acccttccca gaccccagtc agcgcccatc cacccacccc   7620
ttctctgccc ttcagccccc cgggaaacag acgtgcctgt ggataccaac ctcatcgagt   7680
tcgataccaa ctatgccaca gacgatgaca tcgtgtttga ggactttgcc cggctccggc   7740
tgaagggaat gaaggatgat gactgtgatg accagttttg ccatcatcac catcaccatt   7800
agtaagcggc cgcgatcgtg attgtgctgg gccaccacct tggcaaggat ttcacccccg   7860
ctgcacaggc tgccttccag aaggtggtgg ctggagtggc cgctgccctg gctcacaagt   7920
accactaaac cccctttcct gctcttgcct gtgaacaatg gttaattgtt cccaagagag   7980
catctgtcag ttgttggcaa aatgataaag acatttgaaa atctgtcttc tgacaaataa   8040
aaagcattta tttcactgca atgatgtttt aaattatttg tctgtgtcat agaagggttt   8100
atgctaagtt ttcaagatac aaagaagtga gggttcaggt ctgaccttgg ggaaataaat   8160
gaattacact tcaaatgtat gggacagcaa gcagtaagcc acagatccta ttgccatgcc   8220
ctaaacactc agagaaaaat tcaacaaatg gtttcattta tacactacat tatgattaca   8280
ttttatgtaa attatttgtt ttttctactc ttccacataa atgtcttttt ttcctcttac   8340
ctacccagca cttcacagtt ctcaagccaa taatttttct tttgtaaaat taccattatt   8400
ctctaaactt ttccctctgt gtttaccaag caacattatt tatcttttca taaatcctgt   8460
tgccttagac agctccaata gcaatagagg tatgattaag gagagaatag aagtgccctg   8520
tttgtcatac catgcctgca cagtcaatag tcactatgag atttcaaatg gcactttgcc   8580
tgggaccttt acacctcaca ccatactctg gcttgagtta ggagttaaga atgagagaaa   8640
```

tataagatct gtcgac 8656

<210> SEQ ID NO 3
<211> LENGTH: 24
<212> TYPE: DNA
<213> ORGANISM: Artificial Sequence
<220> FEATURE:
<223> OTHER INFORMATION: Rosa domain 5'HR detection primer (Forward)

<400> SEQUENCE: 3
gttctgtgag acagccgggt acga 24

<210> SEQ ID NO 4
<211> LENGTH: 24
<212> TYPE: DNA
<213> ORGANISM: Artificial Sequence
<220> FEATURE:
<223> OTHER INFORMATION: P2Y11_5'HR detection primer (Reverse), genotyping primer

<400> SEQUENCE: 4
gctgatgcag gtgatgaaga tgac 24

<210> SEQ ID NO 5
<211> LENGTH: 24
<212> TYPE: DNA
<213> ORGANISM: Artificial Sequence
<220> FEATURE:
<223> OTHER INFORMATION: P2Y11_3'HR detection primer (Forward)

<400> SEQUENCE: 5
gaggctacaa acgctctcat cgac 24

<210> SEQ ID NO 6
<211> LENGTH: 31
<212> TYPE: DNA
<213> ORGANISM: Artificial Sequence
<220> FEATURE:
<223> OTHER INFORMATION: Rosa domain 3'HR detection primer (Reverse)

<400> SEQUENCE: 6
atcagcctgg caatatgtaa gatacatcag g 31

<210> SEQ ID NO 7
<211> LENGTH: 23
<212> TYPE: DNA
<213> ORGANISM: Artificial Sequence
<220> FEATURE:
<223> OTHER INFORMATION: Arrb_5'HR detection primer (Reverse)

<400> SEQUENCE: 7
agtccctatt ggcgttacta tgg 23

<210> SEQ ID NO 8
<211> LENGTH: 25
<212> TYPE: DNA
<213> ORGANISM: Artificial Sequence
<220> FEATURE:
<223> OTHER INFORMATION: Arrb_3'HR detection primer (Forward)

<400> SEQUENCE: 8
cacctagagg cttccctgga caaag 25

<210> SEQ ID NO 9
<211> LENGTH: 374
<212> TYPE: PRT

```
<213> ORGANISM: Homo sapiens
<220> FEATURE:
<223> OTHER INFORMATION: human P2Y11 amino acid sequence introduced into
      KI mouse

<400> SEQUENCE: 9

Met Ala Ala Asn Val Ser Gly Ala Lys Ser Cys Pro Ala Asn Phe Leu
1               5                   10                  15

Ala Ala Ala Asp Asp Lys Leu Ser Gly Phe Gln Gly Asp Phe Leu Trp
            20                  25                  30

Pro Ile Leu Val Val Glu Phe Leu Val Ala Val Ala Ser Asn Gly Leu
        35                  40                  45

Ala Leu Tyr Arg Phe Ser Ile Arg Lys Gln Arg Pro Trp His Pro Ala
    50                  55                  60

Val Val Phe Ser Val Gln Leu Ala Val Ser Asp Leu Leu Cys Ala Leu
65                  70                  75                  80

Thr Leu Pro Pro Leu Ala Ala Tyr Leu Tyr Pro Pro Lys His Trp Arg
                85                  90                  95

Tyr Gly Glu Ala Ala Cys Arg Leu Glu Arg Phe Leu Phe Thr Cys Asn
            100                 105                 110

Leu Leu Gly Ser Val Ile Phe Ile Thr Cys Ile Ser Leu Asn Arg Tyr
        115                 120                 125

Leu Gly Ile Val His Pro Phe Phe Ala Arg Ser His Leu Arg Pro Lys
    130                 135                 140

His Ala Trp Ala Val Ser Ala Ala Gly Trp Val Leu Ala Ala Leu Leu
145                 150                 155                 160

Ala Met Pro Thr Leu Ser Phe Ser His Leu Lys Arg Pro Gln Gln Gly
                165                 170                 175

Ala Gly Asn Cys Ser Val Ala Arg Pro Glu Ala Cys Ile Lys Cys Leu
            180                 185                 190

Gly Thr Ala Asp His Gly Leu Ala Ala Tyr Arg Ala Tyr Ser Leu Val
        195                 200                 205

Leu Ala Gly Leu Gly Cys Gly Leu Pro Leu Leu Leu Thr Leu Ala Ala
    210                 215                 220

Tyr Gly Ala Leu Gly Arg Ala Val Leu Arg Ser Pro Gly Met Thr Val
225                 230                 235                 240

Ala Glu Lys Leu Arg Val Ala Ala Leu Val Ala Ser Gly Val Ala Leu
                245                 250                 255

Tyr Ala Ser Ser Tyr Val Pro Tyr His Ile Met Arg Val Leu Asn Val
            260                 265                 270

Asp Ala Arg Arg Arg Trp Ser Thr Arg Cys Pro Ser Phe Ala Asp Ile
        275                 280                 285

Ala Gln Ala Thr Ala Ala Leu Glu Leu Gly Pro Tyr Val Gly Tyr Gln
    290                 295                 300

Val Met Arg Gly Leu Met Pro Leu Ala Phe Cys Val His Pro Leu Leu
305                 310                 315                 320

Tyr Met Ala Ala Val Pro Ser Leu Gly Cys Cys Cys Arg His Cys Pro
                325                 330                 335

Gly Tyr Arg Asp Ser Trp Asn Pro Glu Asp Ala Lys Ser Thr Gly Gln
            340                 345                 350

Ala Leu Pro Leu Asn Ala Thr Ala Ala Pro Lys Pro Ser Glu Pro Gln
        355                 360                 365

Ser Arg Glu Leu Ser Gln
    370
```

<210> SEQ ID NO 10
<211> LENGTH: 418
<212> TYPE: PRT
<213> ORGANISM: Mus musculus
<220> FEATURE:
<223> OTHER INFORMATION: mouse Arrb1 amino acid sequence introduced into
KI mouse

<400> SEQUENCE: 10

Met Gly Asp Lys Gly Thr Arg Val Phe Lys Lys Ala Ser Pro Asn Gly
1 5 10 15

Lys Leu Thr Val Tyr Leu Gly Lys Arg Asp Phe Val Asp His Ile Asp
20 25 30

Leu Val Asp Pro Val Asp Gly Val Val Leu Val Asp Pro Glu Tyr Leu
35 40 45

Lys Glu Arg Arg Val Tyr Val Thr Leu Thr Cys Ala Phe Arg Tyr Gly
50 55 60

Arg Glu Asp Leu Asp Val Leu Gly Leu Thr Phe Arg Lys Asp Leu Phe
65 70 75 80

Val Ala Asn Val Gln Ser Phe Pro Pro Ala Pro Glu Asp Lys Lys Pro
85 90 95

Leu Thr Arg Leu Gln Glu Arg Leu Ile Lys Lys Leu Gly Glu His Ala
100 105 110

Cys Pro Phe Thr Phe Glu Ile Pro Pro Asn Leu Pro Cys Ser Val Thr
115 120 125

Leu Gln Pro Gly Pro Glu Asp Thr Gly Lys Ala Cys Gly Val Asp Tyr
130 135 140

Glu Val Lys Ala Phe Cys Ala Glu Asn Leu Glu Glu Lys Ile His Lys
145 150 155 160

Arg Asn Ser Val Arg Leu Val Ile Arg Lys Val Gln Tyr Ala Pro Glu
165 170 175

Arg Pro Gly Pro Gln Pro Thr Ala Glu Thr Thr Arg Gln Phe Leu Met
180 185 190

Ser Asp Lys Pro Leu His Leu Glu Ala Ser Leu Asp Lys Glu Ile Tyr
195 200 205

Tyr His Gly Glu Pro Ile Ser Val Asn Val His Val Thr Asn Asn Thr
210 215 220

Asn Lys Thr Val Lys Lys Ile Lys Ile Ser Val Arg Gln Tyr Ala Asp
225 230 235 240

Ile Cys Leu Phe Asn Thr Ala Gln Tyr Lys Cys Pro Val Ala Met Glu
245 250 255

Glu Ala Asp Asp Asn Val Ala Pro Ser Ser Thr Phe Cys Lys Val Tyr
260 265 270

Thr Leu Thr Pro Phe Leu Ala Asn Asn Arg Glu Lys Arg Gly Leu Ala
275 280 285

Leu Asp Gly Lys Leu Lys His Glu Asp Thr Asn Leu Ala Ser Ser Thr
290 295 300

Leu Leu Arg Glu Gly Ala Asn Arg Glu Ile Leu Gly Ile Ile Val Ser
305 310 315 320

Tyr Lys Val Lys Val Lys Leu Val Val Ser Arg Gly Gly Leu Leu Gly
325 330 335

Asp Leu Ala Ser Ser Asp Val Ala Val Glu Leu Pro Phe Thr Leu Met
340 345 350

His Pro Lys Pro Lys Glu Glu Pro Pro His Arg Glu Val Pro Glu Ser
355 360 365

-continued

```
Glu Thr Pro Val Asp Thr Asn Leu Ile Glu Leu Asp Thr Asn Asp Asp
    370                 375                 380

Asp Ile Val Phe Glu Asp Phe Ala Arg Gln Arg Leu Lys Gly Met Lys
385                 390                 395                 400

Asp Asp Lys Asp Glu Glu Asp Asp Gly Thr Gly Ser Pro His Leu Asn
                405                 410                 415

Asn Arg


<210> SEQ ID NO 11
<211> LENGTH: 421
<212> TYPE: PRT
<213> ORGANISM: Mus musculus
<220> FEATURE:
<223> OTHER INFORMATION: mouse Arrb2 amino acid sequence introduced into
      KI mouse

<400> SEQUENCE: 11

Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
        35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Met Pro Asn Pro Pro Arg
                85                  90                  95

Pro Pro Thr Arg Leu Gln Asp Arg Leu Leu Lys Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Ile Glu Glu Lys Ser His
145                 150                 155                 160

Lys Arg Asn Ser Val Arg Leu Ile Ile Arg Lys Val Gln Phe Ala Pro
                165                 170                 175

Glu Thr Pro Gly Pro Gln Pro Ser Ala Glu Thr Thr Arg His Phe Leu
            180                 185                 190

Met Ser Asp Arg Arg Ser Leu His Leu Glu Ala Ser Leu Asp Lys Glu
        195                 200                 205

Leu Tyr Tyr His Gly Glu Pro Leu Asn Val Asn Val His Val Thr Asn
    210                 215                 220

Asn Ser Ala Lys Thr Val Lys Lys Ile Arg Val Ser Val Arg Gln Tyr
225                 230                 235                 240

Ala Asp Ile Cys Leu Phe Ser Thr Ala Gln Tyr Lys Cys Pro Val Ala
                245                 250                 255

Gln Leu Glu Gln Asp Asp Gln Val Ser Pro Ser Ser Thr Phe Cys Lys
            260                 265                 270

Val Tyr Thr Ile Thr Pro Leu Leu Ser Asp Asn Arg Glu Lys Arg Gly
        275                 280                 285

Leu Ala Leu Asp Gly Gln Leu Lys His Glu Asp Thr Asn Leu Ala Ser
    290                 295                 300
```

```
Ser Thr Ile Val Lys Glu Gly Ala Asn Lys Glu Val Leu Gly Ile Leu
305                 310                 315                 320

Val Ser Tyr Arg Val Lys Val Lys Leu Val Val Ser Arg Gly Gly Asp
                325                 330                 335

Val Ser Val Glu Leu Pro Phe Val Leu Met His Pro Lys Pro His Asp
            340                 345                 350

His Ile Thr Leu Pro Arg Pro Gln Ser Ala Pro Ile His Pro Pro Leu
        355                 360                 365

Leu Cys Pro Ser Ala Pro Arg Glu Thr Asp Val Pro Val Asp Thr Asn
    370                 375                 380

Leu Ile Glu Phe Asp Thr Asn Tyr Ala Thr Asp Asp Asp Ile Val Phe
385                 390                 395                 400

Glu Asp Phe Ala Arg Leu Arg Leu Lys Gly Met Lys Asp Asp Asp Cys
                405                 410                 415

Asp Asp Gln Phe Cys
            420


<210> SEQ ID NO 12
<211> LENGTH: 567
<212> TYPE: DNA
<213> ORGANISM: Artificial Sequence
<220> FEATURE:
<223> OTHER INFORMATION: mutant Kras

<400> SEQUENCE: 12

atgaccgagt acaagctggt ggtcgtgggc gctgacggag tgggcaagtc tgccctgacc     60

atccagctga tccagaacca cttcgtggac gagtacgacc ccaccatcga ggacagctac    120

cggaagcagg tcgtgatcga cggcgagaca tgcctgctgg acatcctgga cacagccggc    180

caggaagagt actccgccat gcgggatcag tacatgcgga ccggcgaagg cttcctgtgc    240

gtgttcgcca tcaacaacac caagagcttc gaggacatcc accactaccg cgagcagatc    300

aagagagtga aggacagcga ggacgtgccc atggtgctcg tgggcaacaa gtgcgacctg    360

cccagccgga ccgtggacac caagcaggcc caggagctgg ccagaagcta cggcatcccc    420

ttcatcgaga caagcgccaa gacccggcag ggcgtggacg acgccttcta caccctcgtg    480

cgcgagatcc ggaagcacaa agaaaaaatg tccaaggacg gcaagaagaa gaagaagaaa    540

tcccggacca gatgcactgt gatgtga                                        567


<210> SEQ ID NO 13
<211> LENGTH: 20
<212> TYPE: DNA
<213> ORGANISM: Artificial Sequence
<220> FEATURE:
<223> OTHER INFORMATION: gRNA targeting Trp53 (exon4)

<400> SEQUENCE: 13

aggagctcct gacactcgga                                                 20


<210> SEQ ID NO 14
<211> LENGTH: 20
<212> TYPE: DNA
<213> ORGANISM: Artificial Sequence
<220> FEATURE:
<223> OTHER INFORMATION: gRNA targeting Trp53 (exon5)

<400> SEQUENCE: 14

gaagtcacag cacatgacgg                                                 20
```

<210> SEQ ID NO 15
<211> LENGTH: 20
<212> TYPE: DNA
<213> ORGANISM: Artificial Sequence
<220> FEATURE:
<223> OTHER INFORMATION: gRNA targeting Trp53 (exon6)

<400> SEQUENCE: 15
acaaaattac agacctcggg 20

<210> SEQ ID NO 16
<211> LENGTH: 20
<212> TYPE: DNA
<213> ORGANISM: Artificial Sequence
<220> FEATURE:
<223> OTHER INFORMATION: gRNA targeting Cdkn2a (p16) (exon2)

<400> SEQUENCE: 16
ctcgacttgg cccaagagcg 20

<210> SEQ ID NO 17
<211> LENGTH: 20
<212> TYPE: DNA
<213> ORGANISM: Artificial Sequence
<220> FEATURE:
<223> OTHER INFORMATION: gRNA targeting Cdkn2a (p16) (exon2)

<400> SEQUENCE: 17
gcagctcttc tgctcaacta 20

<210> SEQ ID NO 18
<211> LENGTH: 20
<212> TYPE: DNA
<213> ORGANISM: Artificial Sequence
<220> FEATURE:
<223> OTHER INFORMATION: gRNA targeting Cdkn2a (p16) (exon1b)

<400> SEQUENCE: 18
ccgctgctgt actccctcag 20

<210> SEQ ID NO 19
<211> LENGTH: 20
<212> TYPE: DNA
<213> ORGANISM: Artificial Sequence
<220> FEATURE:
<223> OTHER INFORMATION: gRNA targeting Smad4 (exon8)

<400> SEQUENCE: 19
caaaagcgat ctcctcccga 20

<210> SEQ ID NO 20
<211> LENGTH: 20
<212> TYPE: DNA
<213> ORGANISM: Artificial Sequence
<220> FEATURE:
<223> OTHER INFORMATION: gRNA targeting Smad4 (exon8)

<400> SEQUENCE: 20
tttgaaatgg acgttcaggt 20

<210> SEQ ID NO 21
<211> LENGTH: 20
<212> TYPE: DNA
<213> ORGANISM: Artificial Sequence
<220> FEATURE:
<223> OTHER INFORMATION: gRNA targeting Smad4 (exon9)

<400> SEQUENCE: 21

```
aactctgtac aaagaccgcg                                                20
```